United States Patent
Bell et al.

(10) Patent No.: US 7,727,768 B2
(45) Date of Patent: Jun. 1, 2010

(54) METHOD FOR A NANOCALORIMETER FOR DETECTING CHEMICAL REACTIONS

(75) Inventors: Alan G. Bell, Palo Alto, CA (US);
Richard H. Bruce, Los Altos, CA (US);
Scott A. Elrod, La Honda, CA (US);
Eric Peeters, Fremont, CA (US);
Francisco E. Torres, San Jose, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 810 days.

(21) Appl. No.: 11/149,632

(22) Filed: Jun. 10, 2005

(65) Prior Publication Data

US 2006/0078999 A1  Apr. 13, 2006

Related U.S. Application Data

(62) Division of application No. 10/114,611, filed on Apr. 1, 2002, now Pat. No. 7,141,210.

(51) Int. Cl.
*G01N 33/00* (2006.01)
(52) U.S. Cl. .................. 436/147; 422/68.1; 422/82.01; 422/99
(58) Field of Classification Search .......... 422/68.1, 422/82.01, 99; 436/147
See application file for complete search history.

(56) References Cited

U.S. PATENT DOCUMENTS

| | | | |
|---|---|---|---|
| 4,731,340 A | 3/1988 | Chang et al. | |
| 5,486,337 A | 1/1996 | Ohkawa | |
| 5,967,659 A | 10/1999 | Plotnikov et al. | 374/11 |
| 6,079,873 A | 6/2000 | Cavicchi et al. | 374/10 |
| 6,096,559 A | 8/2000 | Thundat et al. | 436/147 |
| 6,193,413 B1 | 2/2001 | Lieberman | 374/45 |
| 6,331,074 B1 | 12/2001 | Kimura | |
| 6,380,605 B1 | 4/2002 | Verhaegen | |
| 6,402,369 B1 | 6/2002 | Ludington et al. | |
| 6,436,346 B1 | 8/2002 | Doktycz et al. | |
| 6,545,334 B2 | 4/2003 | Verhaegen | |
| 6,648,503 B2 | 11/2003 | Tanaka et al. | |

(Continued)

FOREIGN PATENT DOCUMENTS

DE  19947788 A1  4/2001

(Continued)

OTHER PUBLICATIONS

Notice of Allowance and Fee(s) Due in U.S. Appl. No. 10/303,500, mailed Dec. 23, 2008, 8 pages, published in PAIR.

(Continued)

*Primary Examiner*—Sam P Siefke
(74) *Attorney, Agent, or Firm*—Leading-Edge Law Group, PLC; Mark W. Hrozenchik

(57) ABSTRACT

A method for detecting chemical reactions uses a nanocalorimeter having a substrate including thermal isolation capability residing on the substrate, thermal equilibration regions residing within the thermal isolation capability, and thermal measurement capability residing within each of the thermal equilibration regions. The thermal measurement device is connected to detection electronics. The method includes depositing drops of potentially reactive chemical solutions within the thermal equilibration region. These potentially reactive solution drops are merged through the use of drop merging electrodes residing within the thermal isolation region. The thermal change occurring within the merged solution drops is then measured with the detection electronics.

16 Claims, 10 Drawing Sheets

U.S. PATENT DOCUMENTS

| | | | |
|---|---|---|---|
| 6,843,596 | B2 | 1/2005 | Verhaegen |
| 7,141,210 | B2 | 11/2006 | Bell et al. |
| 7,147,763 | B2 | 12/2006 | Elrod et al. |
| 7,416,897 | B2 | 8/2008 | Bruce et al. |
| 7,419,835 | B2 | 9/2008 | Torres et al. |
| 7,473,030 | B2 | 1/2009 | Bruce et al. |
| 7,473,031 | B2 | 1/2009 | Wolkin et al. |
| 7,521,253 | B2 | 4/2009 | Bruce et al. |
| 2002/0021740 | A1 | 2/2002 | Danley |
| 2003/0044800 | A1 | 3/2003 | Connelly et al. |
| 2003/0152128 | A1 | 8/2003 | Verhaegen |
| 2003/0183525 | A1 | 10/2003 | Elrod et al. |
| 2003/0186453 | A1 | 10/2003 | Bell et al. |
| 2003/0186454 | A1 | 10/2003 | Bruce et al. |
| 2003/0186455 | A1 | 10/2003 | Bruce et al. |
| 2004/0038227 | A1* | 2/2004 | Verwaerde et al. ............ 435/6 |
| 2004/0038228 | A1 | 2/2004 | Verhaegen |
| 2005/0112710 | A1 | 5/2005 | Torres et al. |
| 2005/0112766 | A1 | 5/2005 | Bruce et al. |
| 2005/0238080 | A1 | 10/2005 | Wolkin et al. |
| 2005/0254552 | A1 | 11/2005 | Bruce et al. |
| 2005/0254994 | A1 | 11/2005 | Bell et al. |
| 2005/0265898 | A1 | 12/2005 | Bell et al. |
| 2007/0145362 | A1 | 6/2007 | Wolkin et al. |
| 2007/0147473 | A1 | 6/2007 | Wolkin et al. |
| 2007/0148416 | A1 | 6/2007 | Wolkin et al. |
| 2008/0304541 | A1 | 12/2008 | Recht et al. |

FOREIGN PATENT DOCUMENTS

| | | | |
|---|---|---|---|
| EP | 1351052 | A2 | 10/2003 |
| EP | 1533609 | A2 | 5/2005 |
| EP | 1739399 | A1 | 1/2007 |
| WO | WO 99/54730 | * | 10/1999 |
| WO | WO 00/79254 | A1 | 12/2000 |
| WO | WO 01/85978 | A2 | 11/2001 |

OTHER PUBLICATIONS

Office communication in U.S. Appl. No. 11/167,612, mailed Nov. 21, 2008, 36 pages, published in PAIR.

Amendment with Information Disclosure in U.S. Appl. No. 11/167,612, submitted Feb. 9, 2009, 11 pages, published in PAIR.

Office communication in U.S. Appl. No. 11/318,975, mailed Apr. 29, 2008, 22 pages, published in PAIR.

Amendment with Information Disclosure in U.S. Appl. No. 11/318,975, submitted Jul. 29, 2008, 17 pages, published in PAIR.

Office communication in U.S. Appl. No. 11/318,975, mailed Oct. 15, 2008, 20 pages, published in PAIR.

Amendment After Final Rejection in U.S. Appl. No. 11/318,975, submitted Dec. 12, 2008, 12 pages, published in PAIR.

Office communication in U.S. Appl. No. 11/318,975, mailed Dec. 24, 2008, 3 pages, published in PAIR.

Amendment with Request for Continued Examination in U.S. Appl. No. 11/318,975, submitted Jan. 15, 2009, 23 pages, published in PAIR.

Office communication in U.S. Appl. No. 11/318,975, mailed Mar. 6, 2009, 19 pages, published in PAIR.

Washizu, M., "Electrostatic Actuation of Liquid Droplets for Microreactor Applications", IEEE Transactions on Industry Applications, vol. 34, No. 4, Jul./Aug. 1998, pp. 732-737.

Pierce, M.M., Raman, C.S., Nall, B.T., "Isothermal Titration Calorimetry of Protein-Protein Interactions", Methods, vol. 19, 1999, pp. 213-221.

Pollack, M.G., Fair, R.B., and Shenderov, A.D., "Electrowetting-based actuation of liquid droplets for microfluidic applicatons", Applied Physics Letters, vol. 77, No. 11, Sep. 11, 2000, pp. 1725-1726.

Jones, T.B., Gunji, M., Washizu, M., Feldman, M.J., "Dielectrophoretic liquid actuation and nanodroplet formation", Journal of Applied Physics, vol. 89, No. 2, Jan. 15, 2001, pp. 1441-1448.

Fowler, J., Moon, H., and Kim, C.-J., "Enhancement of Mixing by Droplet-Based Microfluidics", IEEE, 0-7803-7185-Feb. 2002, pp. 97-100.

Johannessen, E.A., Weaver, J.M.R., Cobbold, P.H., and Cooper, J.M., "Heat conduction nanocalorimeter for pl-scale single cell measurements", Applied Physics Letters, vol. 80, No. 11, Mar. 18, 2002, pp. 2029-2031.

Johannessen, E.A., Weaver, J.M.R., Cobbold, P.H., and Cooper, J.M., "A Suspended Membrane Nanocalorimeter for Ultralow Volume Bioanalysis", IEEE Transactions on Nanobioscience, vol. 1, No. 1, Mar. 2002, pp. 29-36.

Office communication in U.S. Appl. No. 10/303,500, mailed Jun. 30, 2008, 9 pages, published in PAIR.

Amendment with Information Disclosure in U.S. Appl. No. 10/303,500, dated Mar. 26, 2008, 13 pages, published in PAIR.

Office communication in U.S. Appl. No. 11/167,748, mailed Jun. 20, 2008, 13 pages, published in PAIR.

Amendment After Final Rejection in U.S. Appl. No. 11/167,748, dated Aug. 20, 2008, 13 pages, published in PAIR.

Office communication in U.S. Appl. No. 11/167,746, mailed Jun. 27, 2008, 7 pages, published in PAIR.

Office communication in U.S. Appl. No. 11/167,746, mailed Aug. 11, 2008, 2 pages, published in PAIR.

Amendment in U.S. Appl. No. 11/167,746, dated Sep. 2, 2008, 18 pages, published in PAIR.

Office communication in U.S. Appl. No. 11/167,612, mailed May 26, 2009, 11 pages.

Amendment After Final Rejection in U.S. Appl. No. 11/167,612, submitted Jun. 26, 2009, 18 pages.

Office communication in U.S. Appl. No. 11/167,612, mailed Jul. 15, 2009, 3 pages.

Amendment with Request for Continued Examination in U.S. Appl. No. 11/167,612, submitted Aug. 25, 2009, 21 pages.

Amendment in U.S. Appl. No. 11/318,975, submitted May 27, 2009, 26 pages.

Office communication in U.S. Appl. No. 11/318,975, mailed Jul. 1, 2009, 18 pages.

Amendment After Final Rejection in U.S. Appl. No. 11/318,975, submitted Jul. 30, 2009, 21 pages.

Office communication in U.S. Appl. No. 11/318,975, mailed Aug. 13, 2009, 7 pages.

Office communication in U.S. Appl. No. 11/167,635, mailed Jun. 11, 2009, 38 pages.

Amendment in U.S. Appl. No. 11/167,635, submitted Aug. 25, 2009, 24 pages.

Office communication in U.S. Appl. No. 11/318,926, mailed Oct. 30, 2009, 29 pages, published in PAIR.

Office communication in U.S. Appl. No. 11/167,612, mailed Nov. 9, 2009, 11 pages, published in PAIR.

Amendment with Request for Continued Examination in U.S. Appl. No. 11/318,975, submitted Sep. 25, 2009, 27 pages, published in PAIR.

Office communication in U.S. Appl. No. 11/760,236, mailed Feb. 26, 2009, 16 pages, published in PAIR.

Amendment in U.S. Appl. No. 11/760,236, submitted May 19, 2009, 23 pages, published in PAIR.

Notice of Allowance and Fee(s) Due in U.S. Appl. No. 11/760,236, mailed Sep. 4, 2009, 13 pages, published in PAIR.

Torres, F.E., et al, "Enthalpy arrays", National Academy of Sciences of USA, vol. 101, No. 26, Jun. 29, 2004, 6 pages.

Notice of Allowance and Fee(s) Due in U.S. Appl. No. 11/167,635, mailed Jan. 4, 2010, 9 pages, published in PAIR.

Amendment in U.S. Appl. No. 11/318,926, submitted Jan. 26, 2010, 20 pages, published in PAIR.

Amendment in U.S. Appl. No. 11/318,975, submitted Feb. 2, 2010, 29 pages, published in PAIR.

Extended European Search Report, Application No. EP 08157385.9, dated Dec. 17, 2009, 9 pages.

* cited by examiner

METHOD FOR A NANOCALORIMETER FOR DETECTING CHEMICAL REACTIONS

CROSS REFERENCE TO RELATED APPLICATIONS

This is a divisional of U.S. application Ser. No. 10/114,611 filed Apr. 1, 2002, now issued as U.S. Pat. No. 7,141,210, by the same inventors, and claims priority therefrom. This divisional application is being filed in response to a restriction requirement in that prior application and contains re-written and/or additional claims to the restricted subject matter.

The following application, U.S. application Ser. No. 10/115,336, filed Mar. 29, 2002, titled "Apparatus and Method for Using Electrostatic Force to Cause Fluid Movement", now issued as U.S. Pat. No. 7,147,763, is assigned to the same assignee of the present application. The entire disclosure of this application is totally incorporated herein by reference in its entirety.

This invention was made with Government support under HHSN 26600400058C/N01-AI-40058 awarded by NIH. The Government has certain rights in this invention.

INCORPORATION BY REFERENCE

The following U.S. patents are fully incorporated herein by reference: U.S. Pat. No. 5,967,659 ("Ultrasensitive Differential Microcalorimeter with User-selected Gain Setting" to Plotnikov et al.); U.S. Pat. No. 6,079,873 ("Micron-scale Differential Scanning Calorimeter on a Chip" to Cavicchi et al.); U.S. Pat. No. 6,096,559 "Micromechanical Calorimetric Sensor" to Thundat et al.); and U.S. Pat. No. 6,193,413 ("System and Method for an Improved Calorimeter for Determining Thermodynamic Properties of Chemical and Biological Reactions" to Lieberman).

BACKGROUND OF THE INVENTION

This invention relates generally to an apparatus and method for an improved nanocalorimeter, and more specifically, to a system and method for an improved nanocalorimeter for measuring the heat released or absorbed during chemical reactions.

Calorimetry is used to measure enthalpic changes, including enthalpic changes arising from reactions, phase changes, changes in molecular conformation, temperature variations, and other variations of interest that may occur for a particular specimen. By measuring enthalpic changes over a series of conditions, other thermodynamic variables may be deduced. For example, measurements of enthalpy as a function of temperature reveal the heat capacity of a specimen, and titrations of reacting components can be used to deduce the binding constant and effective stoichiometry for a reaction. Calorimetry measurements are useful in a broad variety of applications, including, for example, pharmaceuticals (drug discovery, decomposition reactions, crystallization measurements), biology (cell metabolism, drug interactions, fermentation, photosynthesis), catalysts (biological, organic, or inorganic), electrochemical reactions (such as in batteries or fuel cells), and polymer synthesis and characterization, to name a few. In general, calorimetry measurements can be useful in the discovery and development of new chemicals and materials of many types, as well as in the monitoring of chemical processes. Standard calorimeters require relatively large samples (typically about 0.5 ml to 10 liters) and usually measure one sample at a time. As such, these systems cannot be used to measure very small samples, as might be desired for precious or highly reactive materials. Furthermore, standard calorimeters cannot be used effectively to monitor a large number of reactions of small sample size in parallel, as is required in order to perform studies using combinatorial chemistry techniques.

In recent years, researchers and companies have turned to combinatorial methods and techniques for discovering and developing new compounds, materials, and chemistries. For example, pharmaceutical researchers have turned to combinatorial libraries as sources of new lead compounds for drug discovery. As another example, Symyx Technologies® is applying combinatorial techniques to materials discovery in the life sciences, chemical, and electronics industries. Consequently, there is a need for tools that can measure reactions and interactions of large numbers of small samples in parallel, consistent with the needs of combinatorial discovery techniques. Preferably, users desire that these tools enable inexpensive measurements and minimize contamination and cross-contamination problems.

In some cases, the sample to be studied is precious, and it might not be acceptable to use the relatively large amount of material required by a standard microcalorimeter to perform only one measurement. For example, one may desire to study a natural extract or synthesized compound for biological interactions, but in some cases the available amount of material at concentrations large enough for calorimetry might be no more than a few milliliters. Performing a measurement in standard microcalorimeters, such as those sold, for example, by MicroCal® Inc. (model VP-ITC) or Calorimetry Sciences Corporation® (model CSC-4500), requires about 1 ml of sample, which means that one would possibly be faced with using a majority or all of the precious material for one or a small series of measurements. Tools that enable calorimetric measurements with much smaller sample sizes would be helpful in overcoming this limitation.

One of the most popular uses of combinatorial techniques to date has been in pharmaceutical research. Pharmaceutical researchers have turned to combinatorial libraries as sources of new lead compounds for drug discovery. A combinatorial library is a collection of chemical compounds which have been generated, by either chemical synthesis or biological synthesis, by combining a number of chemical "building blocks" as reagents. For example, a combinatorial polypeptide library is formed by combining a set of amino acids in every possible way for a given compound length (i.e., the number of amino acids in a polypeptide compound). Millions of chemical compounds can theoretically be synthesized through such combinatorial mixing of chemical building blocks.

Once a library has been constructed, it must be screened to identify compounds, which possess some kind of biological or pharmacological activity. For example, screening can be done with a specific biological compound, often referred to as a target that participates in a known biological pathway or is involved in some regulation function. The library compounds that are found to react with the targets are candidates for affecting the biological activity of the target, and hence a candidate for a therapeutic agent.

Through the years, the pharmaceutical industry has increasingly relied on high throughput screening (HTS) of libraries of chemical compounds to find drug candidates. HTS describes a method where many discrete compounds are tested in parallel so that large numbers of test compounds are screened for biological activity simultaneously or nearly simultaneously. Currently, the most widely established techniques utilize 96-well microtitre plates. In this format, 96 independent tests are performed simultaneously on a single 8 cm×12 cm plastic plate that contains 96 reaction wells. These wells typically require assay volumes that range from 50 to 500 μl. In addition to the plates, many instruments, materials, pipettors, robotics, plate washers and plate readers are commercially available to fit the 96-well format to a wide range of homogeneous and heterogeneous assays. To achieve faster testing, the industry is evolving to plates that contain 384 and 1536 wells.

A variety of measurement approaches has been used to screen combinatorial libraries for lead compounds, one of which is the inhibitor assay. In the inhibitor assay, a marker ligand, often the natural ligand in a biological pathway, is identified that will bind well with the target protein molecule. The assay requires the chemical attachment of a fluorescent molecule to this marker ligand such that the fluorescent molecule does not affect the manner in which the marker ligand reacts with the target protein. To operate an inhibitor assay, the target protein is exposed to the test ligands in microtitre wells. After a time necessary for reaction of the test ligand to the target protein, the marker ligand is applied. After a time for reaction with the marker ligand, the wells are rinsed such that non-reacted marker ligand is washed away. In wells where the target protein and the test ligand have reacted, the test ligand blocks the active site of the target protein so the marker ligand cannot react and is washed away, while in cells where the target protein and test ligand have not reacted, the marker ligand reacts with the target protein and is not washed away. By investigating the wells for the presence of fluorescence after the washing, reactions of test ligands and target proteins can be determined as having occurred in wells where no fluorescence is observable.

However, the inhibitor assay requires time and expense to develop the assay. The principal components that need development are discovering a marker ligand and attaching a fluorophore to the marker in a manner that does not affect its reaction with the target protein. Attaching the fluorescent marker can often take 3 months of development or more and cost $250 k or more once the marker ligand is identified. An assay method that avoids such assay development, such as measuring the heat of the reaction with calorimetry, would eliminate this cost and time delay in the discovery process.

Calorimetry measurements are commonly utilized in biophysical and biochemical studies to determine energy changes as indications of biochemical reactions in a media. Prior techniques for measurements include using electrodes, thermopiles, optical techniques, and microcalorimeters for measurements within a sampled media. There is a great interest in developing ultra-miniature microcalorimeter devices that require very small volumes of sampled media for accurate detection and measuring of biochemical reactions on, or in close proximity to, the microcalorimeter and which can be applied in a manner to quickly measure large numbers of reactions such that it can be as efficient as assays such as inhibitor assays which can be used in HTS to screen perhaps 100,000 test ligands a day.

The following disclosures may be relevant and/or helpful in providing an understanding of some aspect of the present invention:

In Plotnikov et al., U.S. Pat. No. 5,967,659 ("Ultrasensitive Differential Microcalorimeter with User-selected Gain Setting"), a differential calorimeter is disclosed that includes sample and reference cells, a thermal shield surrounding the cells, heating devices thermally coupled to the thermal shield and the cells, a temperature monitoring system, and a control system. The temperature monitoring system monitors the temperature of the shield, cell temperatures, and temperature differentials between the cells and the shield. The control system generates output signals for control of the heating devices, with a gain setting and scan rate selected by means of a user interface. Output control signals are functions of input temperature signals and the user-selected gain setting, as well as functions of input temperature signals and the user-selected scan rate using a mapping function stored in memory.

In Cavicchi et al., U.S. Pat. No. 6,079,873 ("Micron-scale Differential Scanning Calorimeter on a Chip"), a differential scanning microcalorimeter produced on a silicon chip enables microscopic scanning calorimetry measurements of small samples and thin films. The chip, fabricated using standard CMOS processes, includes a reference zone and a sample zone. The reference and sample zones may be at opposite ends of a suspended platform or may reside on separate platforms. Each zone is heated with an integrated polysilicon heater. A thermopile consisting of a succession of thermocouple junctions generates a voltage representing the temperature difference between the reference and sample zones.

In Thundat et al., U.S. Pat. No. 6,096,559 ("Micromechanical Calorimetric Sensor"), a calorimeter sensor apparatus utilizes microcantilevered spring elements for detecting thermal changes within a sample containing biomolecules which undergo chemical and biochemical reactions. The spring element includes a bimaterial layer of chemicals on a coated region on at least one surface of the microcantilever. The chemicals generate a differential thermal stress across the surface upon reaction of the chemicals with an analyte or biomolecules within the sample due to the heat of chemical reactions in the sample placed on the coated region. The thermal stress across the spring element surface creates mechanical bending of the microcantilever. The spring element has a low thermal mass to allow detection and measuring of heat transfers associated with chemical and biochemical reactions within a sample place on or near the coated region. Deflections of the cantilever are detected by a variety of detection techniques.

In Lieberman, U.S. Pat. No. 6,193,413 ("System and Method for an Improved Calorimeter for Determining Thermodynamic Properties of Chemical and Biological Reactions") a microcalorimeter includes a thin amorphous membrane anchored to a frame within an environmental chamber. Thermometers and heaters are placed on one side of a thermal conduction layer mounted on the central portion of the membrane. Samples are placed on two such membranes; each sample is heated and its individual heat capacity determined. The samples are then mixed by sandwiching the two microcalorimeters together to cause a binding reaction to occur. The amount of heat liberated during the reaction is measured to determine the enthalpy of binding.

SUMMARY OF THE INVENTION

The disclosed embodiments provide examples of improved solutions to the problems noted in the above Background discussion and the art cited therein. There is shown in these examples an improved method for detecting chemical reactions uses a nanocalorimeter having a substrate including thermal isolation capability residing on the substrate, thermal equilibration regions residing within the thermal isolation capability, and thermal measurement capability residing within each of the thermal equilibration regions. The thermal measurement device is connected to detection electronics. The method includes depositing drops of potentially reactive chemical solutions within the thermal equilibration region. These potentially reactive solution drops are merged through the use of drop merging electrodes residing within the thermal isolation region. The thermal change occurring within the merged solution drops is then measured with the detection electronics.

In another embodiment, there is disclosed a system method for detecting chemical reactions using a nanocalorimeter. The nanocalorimeter includes a substrate having thermal isolation capability, thermal equilibration regions residing within the thermal isolation capability, and thermal measurement capability residing within each of the thermal equilibration regions. The thermal measurement capability is connected to detection electronics. The system enables the user to deposit drops of potentially reactive chemical solutions within the thermal equilibration region. These potentially reactive solution drops are merged through the use of drop merging electrodes residing within the thermal isolation region. The thermal change occurring within the merged solution drops is then measured with the detection electronics.

BRIEF DESCRIPTION OF THE DRAWINGS

The foregoing and other features of the instant invention will be apparent and easily understood from a further reading of the specification, claims and by reference to the accompanying drawings in which:

DETAILED DESCRIPTION OF THE INVENTION

Figure 1:
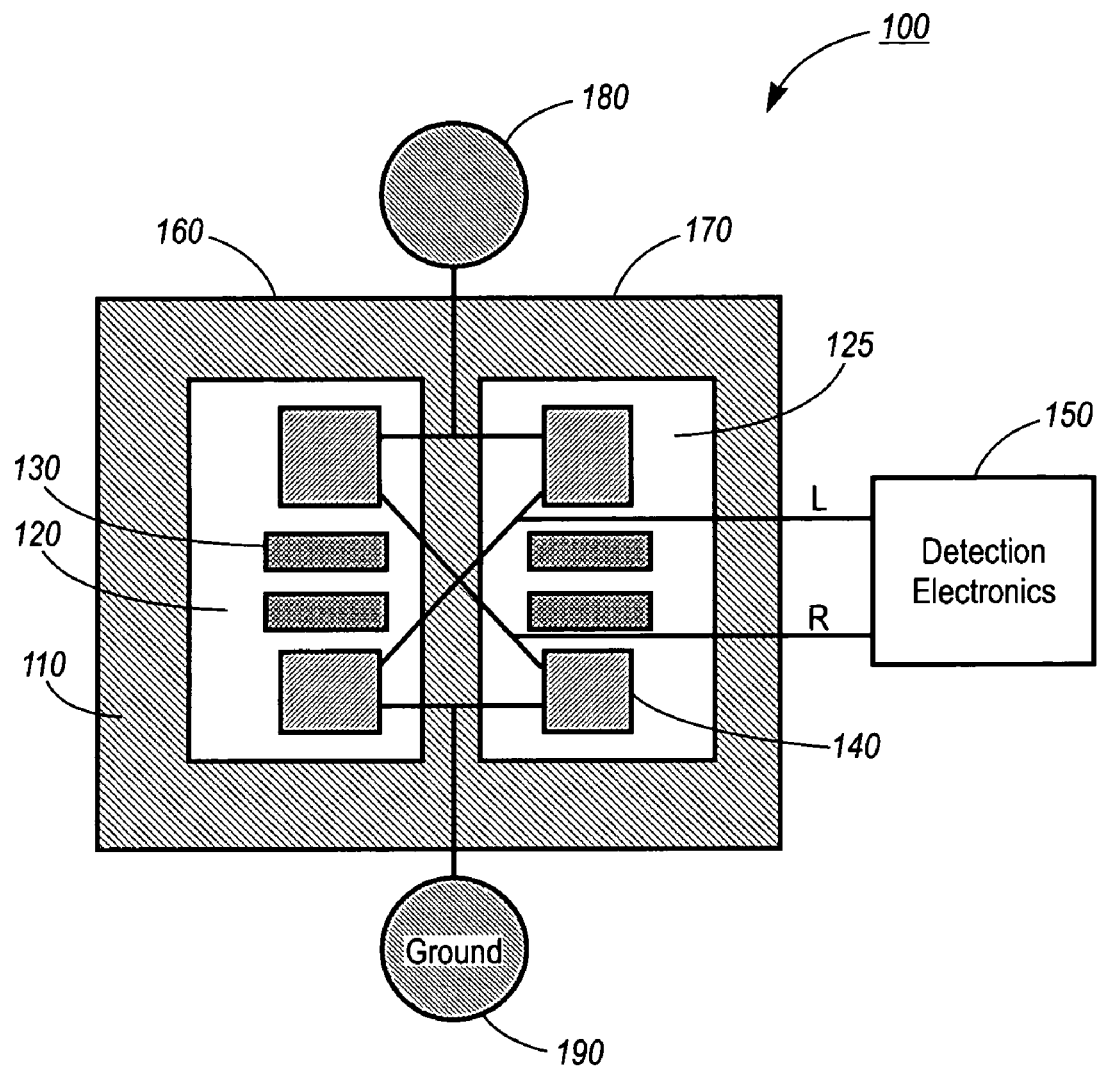
FIG. 1 is a block diagram depicting components of a nanocalorimeter in accordance with one embodiment of the present invention.

As used herein, the term "ligand" refers to an agent that binds a target molecule. In the case in which the target molecule is a target protein, the agent may bind the target protein when the target protein is in its native conformation, or when it is partially or totally unfolded or denatured. According to the present invention, a ligand is not limited to an agent that binds a recognized functional region of the target protein e.g. the active site of an enzyme, the antigen-combining site of an antibody, the hormone-binding site of a receptor, a cofactor-binding site, and the like. In practicing the present invention, a ligand can also be an agent that binds any surface or internal sequences or conformational domains of the target protein. Therefore, the ligands of the present invention encompass agents that in and of themselves may have no apparent biological function, beyond their ability to bind to the target protein in the manner described above.

As used herein, the term "test ligand" refers to an agent, comprising a compound, molecule or complex, which is being tested for its ability to bind to a target molecule. Test ligands can be virtually any agent, including without limitation metals, peptides, proteins, lipids, polysaccharides, nucleic acids, small organic molecules, and combinations thereof. Complex mixtures of substances such as natural product extracts, which may include more than one test ligand, can also be tested, and the component that binds the target molecule can be purified from the mixture in a subsequent step.

As used herein, the term "target protein" refers to a peptide, protein or protein complex for which identification of a ligand or binding partner is desired. Target proteins include without limitation peptides or proteins known or believed to be involved in the etiology of a given disease, condition or pathophysiological state, or in the regulation of physiological function. Target proteins may be derived from any living organism, such as a vertebrate, particularly a mammal and even more particularly a human. For use in the present invention, it is not necessary that the protein's biochemical function be specifically identified. Target proteins include without limitation receptors, enzymes, oncogene products, tumor suppressor gene products, vital proteins, and transcription factors, either in purified form or as part of a complex mixture of proteins and other compounds. Furthermore, target proteins may comprise wild type proteins, or, alternatively, mutant or variant proteins, including those with altered stability, activity, or other variant properties, or hybrid proteins to which foreign amino acid sequences, e.g. sequences that facilitate purification, have been added.

As used herein, "test combination" refers to the combination of a test ligand and a target protein. "Control combination" refers to the target protein in the absence of a test ligand.

As used herein, "screening" refers to the testing of a multiplicity of molecules or compounds for their ability to bind to a target molecule.

As used herein, the term "lead molecule" refers to a molecule or compound, from a combinatorial library, which displays relatively high affinity for a target molecule. High affinity is detected by this invention through the heat released in a chemical reaction. The terms "lead compound" and "lead molecule" are synonymous.

As used herein, the term "target molecule" encompasses peptides, proteins, nucleic-acids, and other receptors. The term encompasses both enzymes and proteins which are not enzymes. The term encompasses monomeric and multimeric proteins. Multimeric proteins may be homomeric or heteromeric. The term encompasses nucleic acids comprising at least two nucleotides, such as oligonucleotides. Nucleic acids can be single-stranded, double-stranded, or triple-stranded. The term encompasses a nucleic acid which is a synthetic oligonucleotide, a portion of a recombinant DNA molecule, or a portion of chromosomal DNA. The term target molecule also encompasses portions of peptides, secondary, tertiary, or quaternary structure through folding, with substituents including, but not limited to, cofactors, coenzymes, prosthetic groups, lipids, oligosaccharides, or phosphate groups.

As used herein, the term "molecule" refers to the compound, which is tested for binding affinity for the target molecule. This term encompasses chemical compounds of any structure, including, but not limited to nucleic acids and peptides. More specifically, the term "molecule" encompasses compounds in a compound or a combinatorial library. The terms "molecule" and "ligand" are synonymous.

As used herein, the term "thermal change" encompasses the release of energy in the form of heat or the absorption of energy in the form of heat.

As used herein, the term "contacting a target molecule" refers broadly to placing the target molecule in solution with the molecule to be screened for binding. Less broadly, contacting refers to the turning, swirling, shaking or vibrating of a solution of the target molecule and the molecule to be screened for binding. More specifically, contacting refers to the mixing of the target molecule with the molecule to be tested for binding. Mixing can be accomplished, for example, by repeated uptake and discharge through a pipette tip or by deposition by robotic means. Preferably, contacting refers to the equilibration of binding between the target molecule and the molecule to be tested for binding.

As used herein, the term "biochemical conditions" encompasses any component, thermodynamic property, or kinetic property of a physical, chemical, or biochemical reaction. Specifically, the term refers to conditions of temperature, pressure, protein concentration, pH, ionic strength, salt concentration, time, electric current, potential difference, and concentrations of cofactor, coenzyme, oxidizing agents, reducing agents, detergents, metal ion, ligands, buffer components, co-solvents including DMSO (dimethyl sulfoxide), glycerol, and related compounds, enhancers, and inhibitors.

The present invention encompasses nanocalorimeters and nanocalorimeter arrays that enable measurement of enthalpic changes, such as enthalpic changes arising from reactions, phase changes, changes in molecular conformation, and the like. Furthermore, the present invention encompasses combinatorial methods and high-throughput screening methods that use nanocalorimeters in the study, discovery, and development of new compounds, materials, chemistries, and chemical processes, as well as high-throughput monitoring of compounds or materials, or high-throughput monitoring of the processes used to synthesize or modify compounds or materials. The present invention also relates to compounds or materials identified by the above methods and their therapeutic uses (for diagnostic, preventive or treatment purposes), uses in purification and separation methods, and uses related to their novel physical or chemical properties. For the purposes herein, a nanocalorimeter refers to a device capable of measuring heats of reaction in the range of nanocalories.

As an example, the present invention encompasses high-throughput screening methods for identifying a ligand that binds a target protein. If the target protein to which the test ligand binds is associated with or causative of a disease or condition, the ligand may be useful for diagnosing, preventing or treating the disease or condition. A ligand identified by the present method can also be one that is used in a purification or separation method, such as a method that results in purification or separation of the target protein from a mixture. The present invention also relates to ligands identified by the present method and their therapeutic uses (for diagnostic, preventive or treatment purposes) and uses in purification and separation methods.

An important feature of the present invention is that it will detect any compound that binds to any sequence or domain of the target protein, not only to sequences or domains that are intimately involved in a biological activity or function. The binding sequence, region, or domain may be present on the surface of the target protein when it is in its folded state, or may be buried in the interior of the protein. Some binding sites may only become accessible to ligand binding when the protein is partially or totally unfolded.

In practicing the present invention, the test ligand is combined with a target protein, and the mixture is maintained under appropriate conditions and for a sufficient time to allow binding of the test ligand to the target protein. Experimental conditions are determined empirically for each target protein. When testing multiple test ligands, incubation conditions are usually chosen so that most ligand:target protein interactions would be expected to proceed to completion. In high-throughput screening applications, the test ligand is usually present in molar excess relative to the target protein. The target protein can be in a soluble form, or, alternatively, can be bound to a solid phase matrix. The matrix may comprise without limitation beads, membrane filters, plastic surfaces, or other suitable solid supports.

Binding to a given protein is a prerequisite for pharmaceuticals intended to modify directly the action of that protein. Thus, if a test ligand is shown, through use of the present method, to bind a protein that reflects or affects the etiology of a condition, it may indicate the potential ability of the test ligand to alter protein function and to be an effective pharmaceutical or lead compound for the development of such a pharmaceutical. Alternatively, the ligand may serve as the basis for the construction of hybrid compounds containing an additional component that has the potential to alter the protein's function. For example, a known compound that inhibits the activity of a family of related enzymes may be rendered specific to one member of the family by conjugation of the known compound to a ligand, identified by the methods of the present invention, that binds specifically to that member at a different site than that recognized by the known compound.

The fact that the present method is based on physicochemical properties common to most proteins gives it widespread application. The present invention can be applied to large-scale systematic high-throughput procedures that allow a cost-effective screening of many thousands of test ligands. Once a ligand has been identified by the methods of the present invention, it can be further analyzed in more detail using known methods specific to the particular target protein used. Also, the ligand can be tested for its ability to influence, either positively or negatively, a known biological activity of the target protein.

Referring now to FIG. 1, there is shown a plan view of one embodiment of detector 100 that is a part of the nanocalorimeter array in accordance with the present invention. This example embodiment enables a passive thermal equilibration of the combined protein, water and ligand drops with the device so that the resultant temperature changes can be detected by means of a temperature sensing device. Because the measurement region is kept small enough and sufficiently thermally conductive, through the fabrication of a thermally conducting layer such as aluminum or copper, the passive equilibration time can be made small. Suitable thermometer elements are based on thin film materials and include but are not limited to resistive thermometers, thermopiles and surface acoustic wave devices (SAW). The preferred embodiment is based on resistive thermometers made from thin film materials with a high temperature coefficient of resistivity, for example amorphous silicon, Vanadium Oxide and Yttrium Barium Copper Oxide (YBCO).

Nanocalorimeter 100 includes thermal isolation layer 110, which contains measurement region 160 and reference region 170. Regions 160 and 170 may also be contained in separate isolation regions, as described hereinbelow. Thermal isolation region 110 provides isolation from surrounding thermal environments, thus increasing measurement time and reducing thermal noise. Although layer 110 is used in this example embodiment to thermally isolate the reaction and temperature sensing components of the nanocalorimeter 100, any means to thermally isolate these components can be used in alternate embodiments of the present invention.

In this example embodiment, the thermal isolation layer 110 may comprise a plastic material in thin foil form (typically ranging from less than 15 microns to approximately 25 microns in thickness for this embodiment, possibly as thin as 2 microns and as thick as 500 microns for some applications). Candidate plastic materials include polyimide (for example Dupont Kapton® and others), polyester (for example Dupont Mylar®) foil, PolyEtherEtherKetone (PEEK), or PolyPhenylene Sulphide (PPS). Alternatively, in embodiments, the thermal isolation region comprises other thin membranes of sufficiently low thermal conductivity, such as SiN and comparable materials.

Measurement region 160 and reference region 170 include thermal equilibrium regions 120 and 125 respectively that are thermally isolated from the detector's mechanical support. In this example embodiment, thermal equilibrium region 120 contains two resistive thermometers 140, which measure the reaction temperature, while thermal equilibrium region 125 contains a second set of two thermometers 140, which measure the variations in the background temperature. The resistive thermometers are deposited in thermal equilibrium regions 120 using standard fabrication techniques, including in embodiments, but not limited to, lithographic patterning of thin films, micro-electronic fabrication techniques (e.g. including sputtering, chemical etching, evaporation), and printed circuit board fabrication techniques. Both thermal equilibrium regions 120 and 125 are sufficiently large to receive and support separate drops of protein and ligand deposited by direct printing and also to support the combination of these two drops after merging, triggered by an example drop merging device 130. For example, for a 400 nL final drop size, the detector, which includes the measurement and reference regions, may be 3.7 mm by 4.6 mm. Each thermal equilibration region 120 and 125 has a sufficient thermal conduction for the region to equilibrate quickly relative to the thermal dissipation. The regions have a sufficiently low heat capacity such that little of the heat of reaction is absorbed in the support. High thermal conductivity with low heat capacity may be accomplished, for example, with a metal film such as a 10 μm thick aluminum or copper film extending over the area of the thermal equilibration region. In this example, for a 400 nL drop and a 10 μm thick aluminum film, the film absorbs approximately 7% of the heat of reaction.

As suggested above, the thermal equilibration regions must be thermally isolated from their environment so that the temperature difference caused by the reaction takes a relatively long time to dissipate. The longer this dissipation time, the longer the signal can be integrated during measurement, which improves the signal to noise ratio. For example, a 10 second integration time corresponds to a 0.1 Hz measurement bandwidth and increases the signal to noise ratio by 3.2 over a 1 second integration. Thermal dissipation occurs through four different channels: conduction across the supporting medium, conduction through the electrical interconnect, conduction through the surrounding environment and evaporation. For the example of conduction across the thermal isolation medium 110, the rate of heat transfer from the drop equals the thermal conductivity of the medium 110 multiplied by the cross section of the medium 110 through which the heat is conducted and the temperature gradient across the region, or $$Q = \Lambda A dT/dx,$$

where $\Lambda$ is the thermal conductivity of the membrane, A is the cross section of the region through which the heat is conducted and $dT/dx$ is the temperature gradient across the thermal isolation medium 110. Note $Q = C\, dT/dt$ where C is the heat capacity of the drop, and from this $$T = T_o e^{-\Lambda A t/CL},$$

where t is the time, L is the length of the isolation region 110, all temperatures are relative to the temperature of the surrounding environment, with the approximation $dT/dx = T/L$. The time constant, $\tau$, for thermal dissipation is therefore $$\tau = CL/\Lambda A.$$

Consequently, the time constant increases with increases in the heat capacity of the drop and decreases with increases in the rate of thermal conduction. Note that while the heat capacity of the drop increases with drop size, increasing the drop size reduces the density of detectors on an array of detectors, increases the thermal equilibration time for the drop, and uses valuable material. A lower array density means a larger array size for a given detector number.

In the example embodiment, drop size is 400 nL for the combined drop after merging. For this drop size, estimates of the time constants associated with different dissipation channels in the example embodiment are shown in the following table:

TABLE 1

| | Time |
|---|---|
| Conduction across thermal isolation layer + interconnect leads | 110 sec |
| Conduction through vapor (Xe) | 19 sec |
| Evaporation (5° C. operation) | 25 sec |

For the purposes of the table, it was assumed that the thermal isolation layer is 7 μm thick plastic and there are eleven interconnect leads with thickness of 0.1 μm for each thermal equilibrium region. As mentioned above, the thermal isolation layer for this embodiment may be fabricated of a plastic material in thin foil form (typically ranging from less than 15 microns to approximately 25 microns in thickness for this embodiment, possibly as thin as 2 microns and as thick as 500 microns for some applications), thereby ensuring that the above time constant for conduction across the thermal isolation layer is large compared with the measurement bandwidth. Examples of candidate plastic materials include polyimide (for example Dupont Kapton® and others), polyester (for example Dupont Mylar®) foil, PolyEtherEtherKetone (PEEK), PolyPhenylene Sulphide (PPS), polyethylene, or polypropylene. In the example embodiment, the same material is also used as the support for the thermal equilibration region, including the resistive thermometers.

In the example embodiment, the same material may be used for the support and the thermal equilibration, including the resistive thermometers. Consequently, one important consideration in selecting a substrate polymer is the highest temperature that is needed in subsequent deposition and processing of thermometer, conductor and insulator films in the particular embodiment. As an example, the temperature needed in the deposition of amorphous silicon thermometer material is typically in the range of 170-250° C. This requires the selection of a substrate polymer film with a high softening temperature. These polymers may include, but are not limited to, polyimide (PI), PolyEtherEtherKetone (PEEK), or PolyPhenylene Sulphide (PPS). Conversely, deposition of Vanadium Oxide thermometer material can be done at a substantially lower temperature. This allows the selection of substrate polymers with a lower softening point, such as Polyester (Dupont Mylar®).

These plastic substrates enable low cost manufacturing that can scale to large arrays of detectors, which enable fast and cost effective testing of large numbers of reactions. This invention anticipates, for example, detector array sizes of 96, 384, 1536 and larger. The low-cost detector arrays might also be used once and then discarded, eliminating time-consuming washing steps and reducing problems with cross-contamination.

Another thermal consideration is the characteristic time for a drop to equilibrate with the detector after it is placed on the detector. This is a combination of the characteristic time for conduction of heat through the drop, $t_1$, and the characteristic conduction time across the detector, $t_2$. In an example embodiment, an aluminum film is used to increase the thermal conduction across the detector. An estimate of the characteristic time $t_1$ is $$t_1 = 0.44 R^2/\alpha = 0.61 \text{ sec,}$$

where R is the drop radius, in this example 460 μm, and α is the thermal diffusivity of the drop, 0.0015 cm²/sec for water. For thin plastic substrates, the characteristic time for lateral conduction across the detector is governed by conduction across the metal film incorporated into the design for temperature equilibration, which is an aluminum strip in this example. An estimate for this characteristic time is $$t_2 = (\rho C_p V)_{drop} \times L_{Al}/4R_{drop} \times \delta \times k_{Al} = 0.44 \text{ sec,}$$

where ρ is the density of the drop, 1 g/cm³ in this example, $C_P$ is the specific heat, 1 cal/g° C. in this example, $L_{Al}$ is the length of the conduction path along the aluminum strip from one drop to the other, 2.5 $R_{drop}$ in this example, δ is the aluminum strip thickness, 10 μm in this example, and $k_{Al}$ is the aluminum thermal conductivity, 0.57 Cal/C—Cm-sec. The aluminum thickness is selected to provide sufficient thermal conduction without contributing significantly to the heat capacity of the detector. Heat capacity of the detector must be made sufficiently low so as to minimize the absorption of heat released from the reaction in the drop in order to minimize attenuation of the temperature change arising from the reaction.

Each thermal equilibration region 120 and 125 contains thermometers 140 and drop merging electrodes 130. Although for the purposes herein thermometers 140 are shown spaced apart from more centrally-positioned drop merging electrodes 130 on each thermal equilibration region 120 and 125, this configuration is for means of example only. Provided that the drop merging device 130 and thermometers 140 are in good thermal contact with the high conductance film, the exact placement of thermometers 140 and drop merging electrodes 130 is not important for thermal considerations.

In operation, the two resistive thermometers 140 situated in thermal equilibration region 120 detect the heat of reaction between an arbitrary protein and a ligand at low concentrations deposited within thermal equilibration region 120. In this example, the heat of reaction is detected through measurement of a voltage change in a bridge circuit due to the resistance change in the thermometers which are configured in the bridge circuit. Resistive thermometers 140 in thermal equilibrium region 120 detect a reaction between a sample ligand and a protein; the other resistive thermometers 145 in thermal equilibrium region 125 serve as a reference. Because the temperature rise due to the reaction may be small, for example approximately 10 μ° C. for protein and ligand concentrations of 1 μM and a heat of reaction of 10⁴ cal/mol, the resistive thermometers 140 are fabricated from materials that provide a large change in resistance for a small temperature change.

In this example embodiment, the resistive thermometers 140 are fabricated from materials with a high temperature coefficient of resistance, such as amorphous silicon Vanadium Oxide and Yttrium Barium Copper Oxide (YBCO). Similar small drops of non-reactive solution (for example water or mixtures of water and DMSO) and target protein, the control combination, are deposited close together in thermal equilibrium region 125. Resistive thermometers 140 are configured as an AC bridge represented by AC generator 180 and ground 190, discussed in more detail hereinbelow. At a specified time after the drops have reached thermal equilibrium, they are moved together to initiate the reaction. The movement operation creates sufficient mixing of the two drops in a time small compared to the measurement time. The heat released by the protein-ligand reaction of the test combination causes a change in the resistance of the affected thermometers relative to the reference thermometers. This change in resistance causes the voltage at the detection point to change from zero. This change is detected by sensitive, noise rejecting circuits such as a lock-in amplifier.

Figure 2:
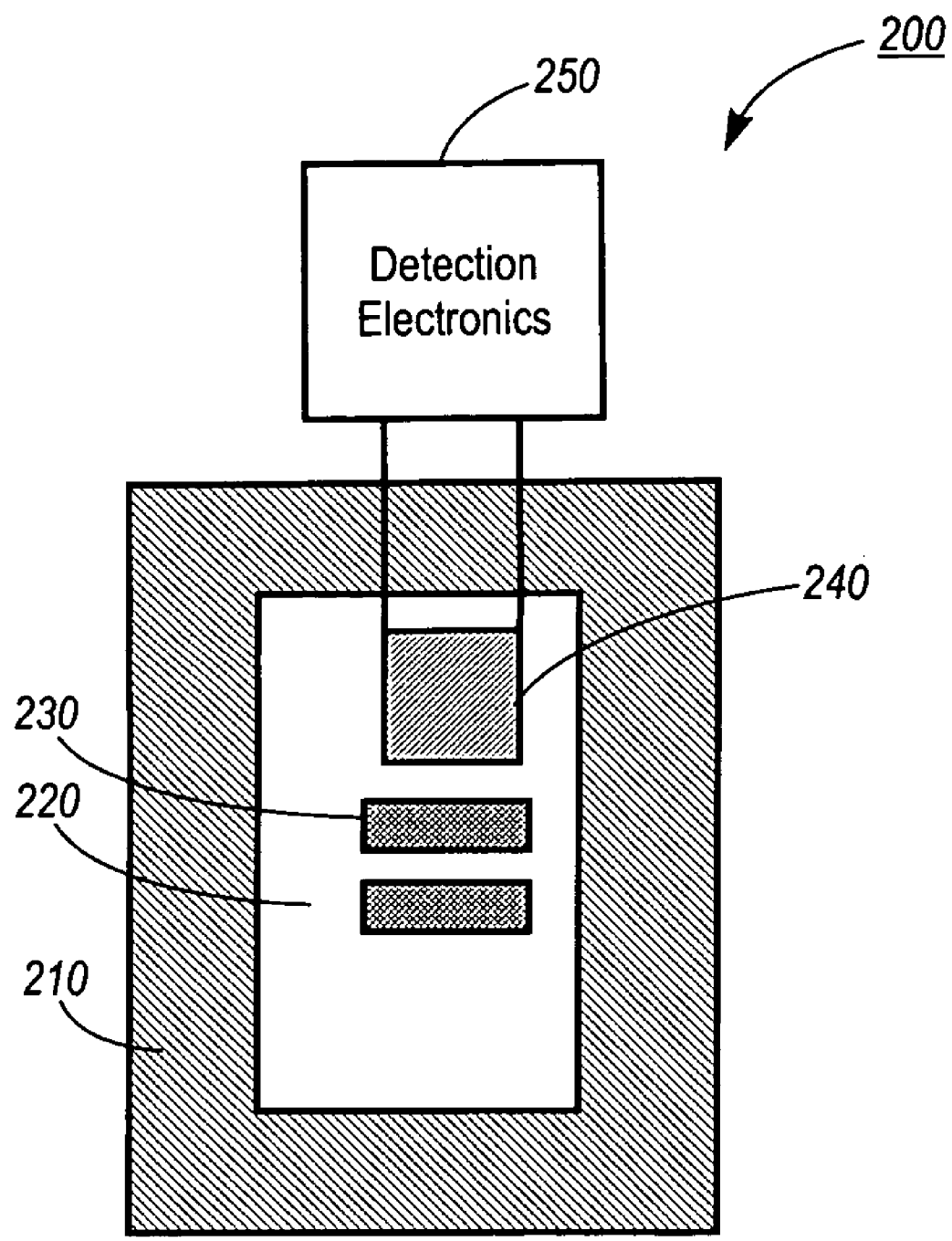
FIG. 2 is a block diagram depicting components of a nanocalorimeter in accordance with another embodiment of the present invention.

Referring now to FIG. 2, there is shown another example embodiment of the present invention. In this example embodiment, nanocalorimeter 200 includes thermal isolation layer 210, which contains thermal equilibrium region 220. Thermal isolation region 210 provides isolation from surrounding thermal environments, thus increasing measurement time and reducing thermal noise. In this example embodiment, thermal equilibrium region 220 contains one resistive thermometer 240, which measures the reaction temperature. The resistive thermometer is deposited in thermal equilibrium region 220 using standard fabrication techniques, including in embodiments, but not limited to, lithographic patterning of thin films, micro-electronic fabrication techniques (e.g. including sputtering, chemical etching, evaporation), and printed circuit board fabrication techniques. Thermal equilibrium region 220 is sufficiently large to receive and support separate drops of protein and ligand deposited by direct printing and also to support the combination of these two drops after merging, triggered by drop merging device 230. Thermal equilibrium region 220 has a sufficient thermal conduction for the region to equilibrate quickly relative to the thermal dissipation. The region also has a sufficiently low heat capacity such that little of the heat of reaction is absorbed in the support. High thermal conductivity with low heat capacity may be accomplished, for example, with a metal film such as a 10 μm thick aluminum or copper film.

Thermal equilibration region 220 contains thermometer 240 and drop merging device 230. Although for the purposes herein thermometer 240 is shown spaced apart from more centrally-positioned drop merging device 230 on thermal equilibration region 220, this configuration is for means of example only. Provided that the drop merging device 230 and thermometer 240 are in good thermal contact with the high conductance film, the exact placement of thermometer 240 and drop merging device 230 is not important for thermal considerations.

In operation, the resistive thermometer 240 situated in thermal equilibration region 220 detects the heat of reaction between an arbitrary protein and a ligand at low concentrations deposited within thermal equilibration region 220. In this example, the heat of reaction is detected through measurement of a voltage change in a bridge circuit due to the resistance change in the thermometer, which is configured in the bridge circuit. Resistive thermometer 240 in thermal equilibrium region 220 detects a reaction between a sample ligand and a protein. Because the temperature rise due to the reaction may be small, for example approximately 1 m° C. for this embodiment, resistive thermometer 240 is fabricated from materials that provide a large change in resistance for a small temperature change. In this example embodiment, resistive thermometer 240 is made of a material with a high temperature coefficient for resistance such as amorphous silicon, Vanadium Oxide and Yttrium Barium Copper Oxide (YBCO).

Resistive thermometer 240 is configured as an AC bridge represented by detection electronics 250, discussed in more detail hereinbelow. The other three legs of the AC bridge are made of low temperature coefficient resistors located on the amplifier printed circuit board. At a specified time after the drops have reached thermal equilibrium, they are moved together to initiate the reaction. The movement operation creates sufficient mixing of the two drops in a time small compared to the measurement time. The heat released by the protein-ligand reaction of the test combination causes a change in the resistance of thermometer 240. This change in resistance causes voltage at a detection point to change from zero. This change is detected by sensitive, noise rejecting circuits such as a lock-in amplifier. Alternatively if the reactions to be measured produce enough heat, the resistance change of the thermometer may be measured by a direct DC resistance measurement.

Figure 3:
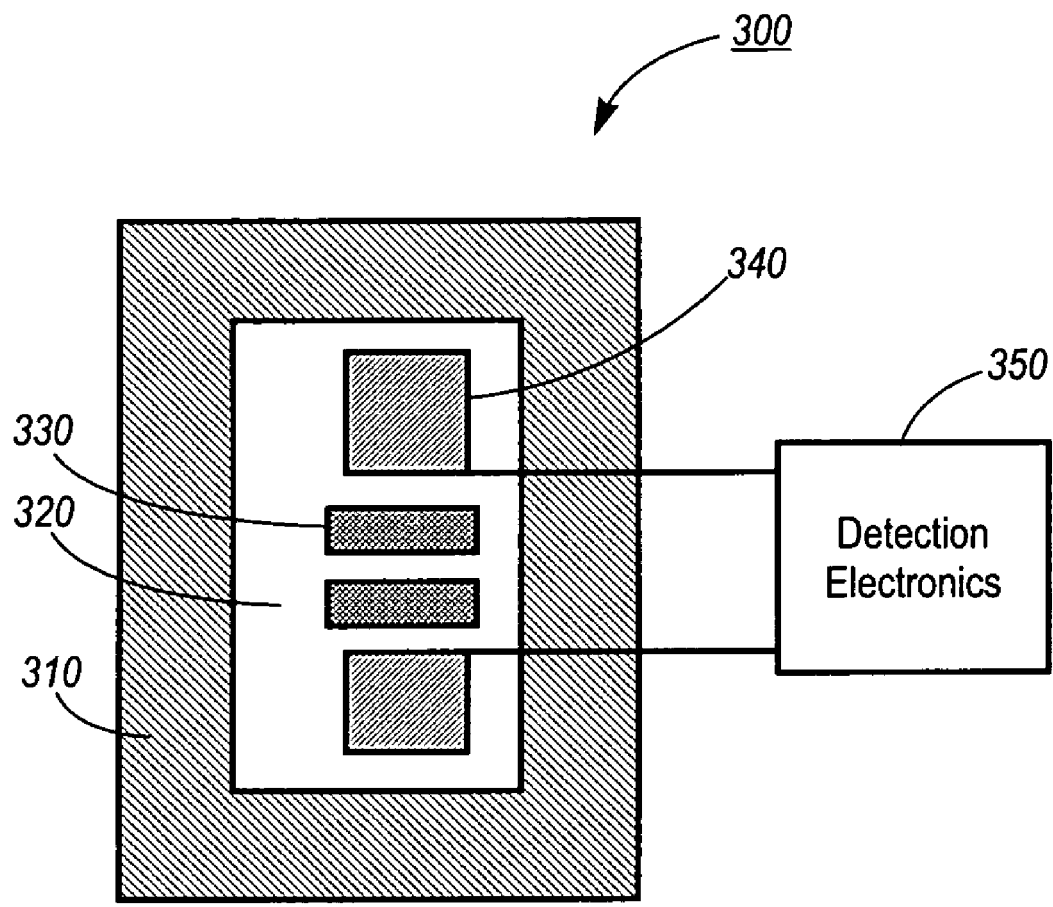
FIG. 3 is a block diagram depicting components of a nanocalorimeter in accordance with yet another embodiment of the present invention.

Referring now to FIG. 3, there is shown another example embodiment of the present invention. In this example embodiment, nanocalorimeter 300 includes thermal isolation layer 310, which contains thermal equilibration region 320. Thermal isolation region 310 provides isolation from surrounding thermal environments, thus increasing measurement time and reducing thermal noise. In this example embodiment, thermal equilibration region 320 contains two resistive thermometers 340, which measure the reaction temperature. Each resistive thermometer is deposited in thermal equilibration region 320 using standard fabrication techniques, including in embodiments, but not limited to, lithographic patterning of thin films, micro-electronic fabrication techniques (e.g. including sputtering, chemical etching, evaporation), and printed circuit board fabrication techniques. Thermal equilibration region 320 is sufficiently large to receive and support separate drops of protein and ligand deposited by direct printing and also to support the combination of these two drops after merging, triggered by drop merging device 330. Thermal equilibration region 320 has a sufficient thermal conduction for the region to equilibrate quickly relative to the thermal dissipation. The region also has a sufficiently low heat capacity such that little of the heat of reaction is absorbed in the support. High thermal conductivity with low heat capacity may be accomplished, for example, with a metal film such as a 10 μm thick aluminum or copper film.

Thermal equilibration region 320 contains thermometers 340 and drop merging device 330. Although for the purposes herein thermometers 340 are shown spaced apart from more centrally-positioned drop merging device 330 on thermal equilibration region 320, this configuration is for means of example only. Provided that the drop merging device 330 and thermometers 340 are in good thermal contact with the high conductance film, the exact placement of thermometers 340 and drop merging device 330 is not important for thermal considerations.

In operation, two resistive thermometers 340 situated in thermal equilibration region 320 detect the heat of reaction between an arbitrary protein and a ligand at low concentrations deposited within thermal equilibration region 320. In this example, the heat of reaction is detected through measurement of a voltage change in a bridge circuit due to the resistance change in the thermometers, which are configured in the bridge circuit. Resistive thermometer 340 in thermal equilibrium region 320 detects a reaction between a sample ligand and a protein. Because the temperature rise due to the reaction may be small, for example approximately 10 μ° C. for protein and ligand concentrations of 1 μM and a heat of reaction of $10^4$ cal/mol, resistive thermometers 340 are fabricated from materials that provide a large change in resistance for a small temperature change. In this example embodiment, resistive thermometers 340 are made of materials with a high temperature coefficient for resistance such as amorphous silicon, Vanadium Oxide and Yttrium Barium Copper Oxide (YBCO).

Resistive thermometer 340 are configured as an AC bridge represented by detection electronics 350, discussed in more detail hereinbelow. The other two legs of the AC bridge are made of low temperature coefficient resistors located on the amplifier printed circuit board. At a specified time after the drops have reached thermal equilibrium, they are moved together to initiate the reaction. The movement operation creates sufficient mixing of the two drops in a time small compared to the measurement time. The heat released by the protein-ligand reaction of the test combination causes a change in the resistance of thermometers 340. This change in resistance causes voltage at a detection point to change from zero. This change is detected by sensitive, noise rejecting circuits such as a lock-in amplifier. Alternatively, if the reactions to be measured produce enough heat, the resistance change of the thermometer may be measured by direct DC resistance measurement of the two thermometers connected in series.

Figure 4:
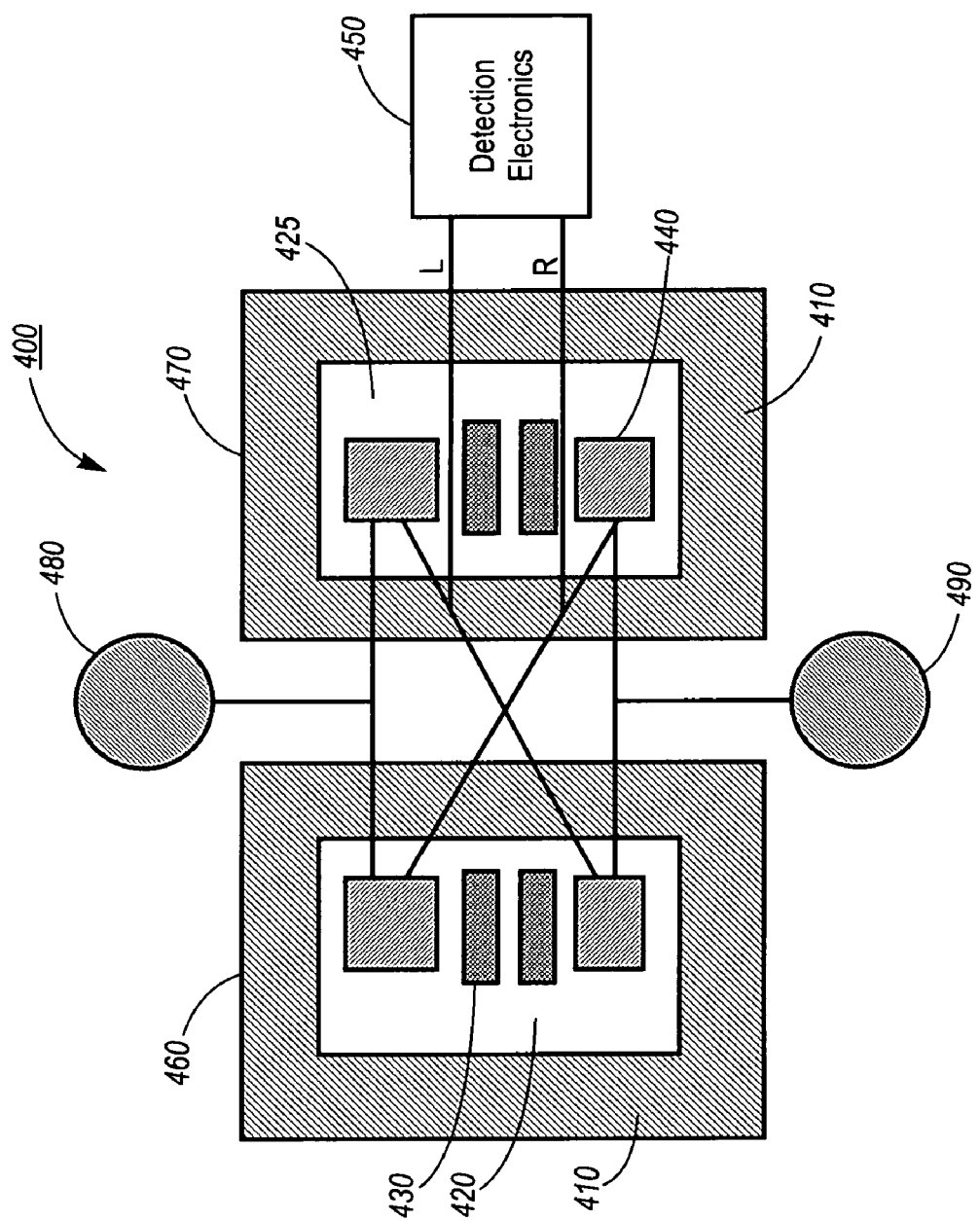
FIG. 4 is a block diagram depicting components of a nanocalorimeter in accordance with yet another embodiment of the present invention.

Referring now to FIG. 4, there is shown yet another example embodiment of the present invention. In this example embodiment, nanocalorimeter 400 includes thermal isolation layers 410, each of which contains a thermal equilibration region. Thermal isolation regions 410 provide isolation from surrounding thermal environments, thus increasing measurement time and reducing thermal noise. In this example embodiment, thermal equilibration regions 420 and 425 each contain two resistive thermometers 440, which measure the reaction temperature. Each resistive thermometer is deposited in thermal equilibration regions 420 and 425 using standard fabrication techniques, including in embodiments, but not limited to, lithographic patterning of thin films, microelectronic fabrication techniques (e.g. including sputtering, chemical etching, evaporation), and printed circuit board fabrication techniques. Thermal equilibration regions 420 and 425 are sufficiently large to receive and support separate drops of protein and ligand deposited by direct printing and also to support the combination of these two drops after merging, triggered by drop merging device 430. Thermal equilibration regions 420 and 425 have a sufficient thermal conduction for the region to equilibrate quickly relative to the thermal dissipation. The regions also have a sufficiently low heat capacity such that little of the heat of reaction is absorbed in the support. High thermal conductivity with low heat capacity may be accomplished, for example, with a metal film such as a 10 μm thick aluminum or copper film.

Thermal equilibration regions 420 and 425 contain thermometers 440 and drop merging devices 430. Although for the purposes herein thermometers 440 are shown spaced apart from more centrally-positioned drop merging device 430 on thermal equilibration regions 420 and 425, this configuration is for means of example only. Provided that the drop merging devices 430 and thermometers 440 are in good thermal contact with the high conductance film, the exact placement of thermometers 440 and drop merging devices 430 is not important for thermal considerations.

In operation, the two resistive thermometers 440 situated in thermal equilibration regions 420 and 425 detect the heat of reaction between an arbitrary protein and a ligand at low concentrations deposited within thermal equilibration regions 420 and 425. The two resistive thermometers 440 situated in thermal equilibration region 425 detect the temperature of drops deposited and merged within thermal equilibration region 420. In this example, the heat of reaction is detected through measurement of a voltage change in a bridge circuit due to the resistance change in the thermometers which are configured in the bridge circuit. Resistive thermometers 440 in thermal equilibration region 420 detect a reaction between a sample ligand and a protein; the other resistive thermometers 440 in thermal equilibration region 425 serve as a reference. Because the temperature rise due to the reaction may be small, for example approximately 10 µ° C. for protein and ligand concentrations of 1 µM and a heat of reaction of $10^4$ cal/mol, the resistive thermometers 440 are fabricated from materials that provide a large change in resistance for a small temperature change. In this example embodiment, the resistive thermometers 440 are made of materials with a high temperature coefficient for resistance such as amorphous silicon, Vanadium Oxide, and Yttrium Barium Copper Oxide (YBCO). Similar small drops of non-reactive solution (for example water or mixtures of water and DMSO) and target protein, the control combination, are deposited close together in thermal equilibrium region 425.

Resistive thermometers 440 are configured as an AC bridge represented by AC generator 480 and ground 490, discussed in more detail hereinbelow. At a specified time after the drops have reached thermal equilibrium, they are moved together to initiate the reaction. The movement operation creates sufficient mixing of the two drops in a time small compared to the measurement time. The heat released by the protein-ligand reaction of the test combination causes a change in the resistance of the affected thermometers. This change in resistance causes the voltage at the detection point to change from zero. This change is detected by sensitive, noise rejecting circuits, for example a lock-in amplifier.

Figure 5:
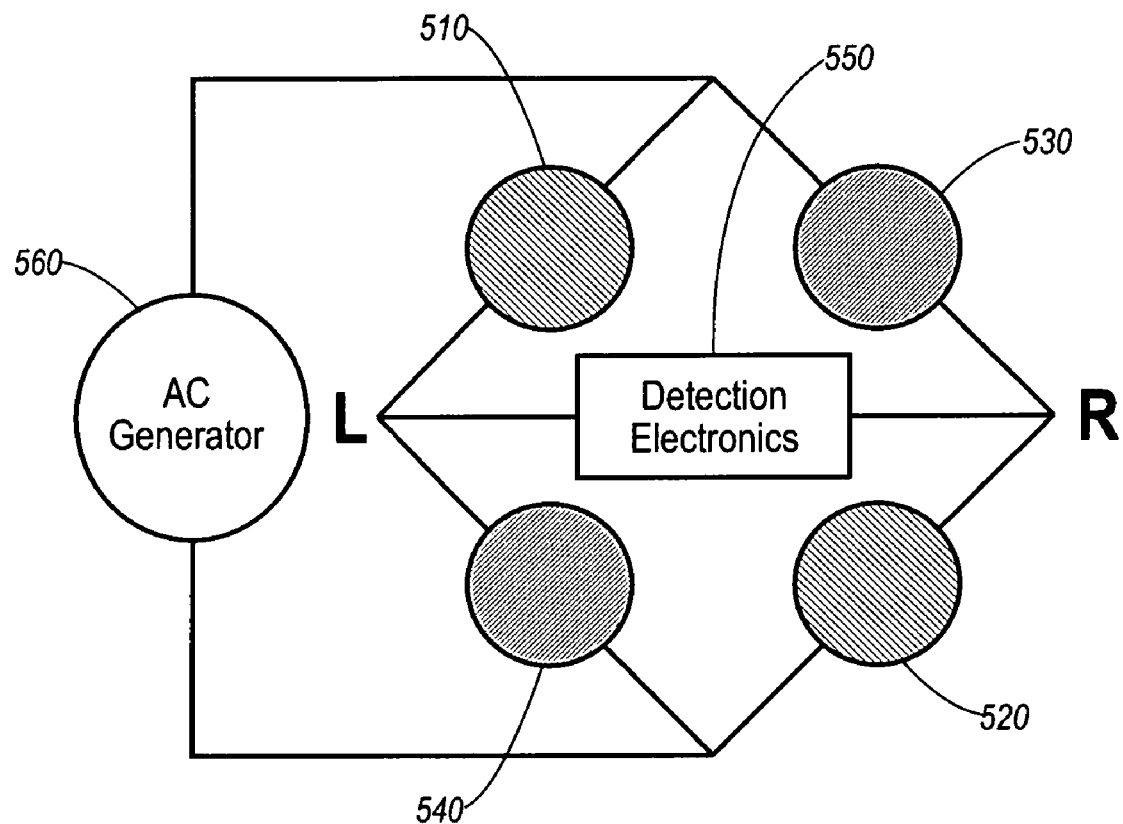
FIG. 5 is a diagram of the arrangement of the measurement thermometers and reference thermometers according to the present invention.

Referring now to FIG. 5, thermometers 510, 520, 530 and 540 form the four resistive legs of one example configuration for a bridge circuit according to the present invention. Resistive thermometers simultaneously measure temperature changes due to both the reaction and the background drift. In this example, two measurement thermometers 530 and 540 measure the reaction and two reference thermometers 510 and 520 measure the background temperature changes. If the resistance of the measurement thermometers changes, as happens when the temperature in the measurement region increases, then the voltage at point R in the bridge becomes more positive or negative relative to ground, depending on the polarity of the voltage placed across the bridge circuit and the sign of the thermal coefficient of resistance, while the voltage at point L in the bridge does the opposite, that is, becomes less positive or negative relative to ground, respectively. This configuration maximizes the voltage difference across detection electronics 550. As will be appreciated by one skilled in the art, other bridge configurations are possible, such as one in which thermometer 540 has a low temperature sensitivity and is not fabricated on the device and where 520 is a variable resistor used to balance the bridge and is also not fabricated on the device.

Resistance thermometers 510, 520, 530 and 540 may be fabricated from patterned thin film and are connected as a bridge. The resistance of each thermometer varies with temperature by an amount proportional to the thermal coefficient of resistance of the material used. Since $$\alpha = 1/R \Delta R/\Delta T,$$

it follows that $$\Delta R = \Delta R \Delta T,$$

where R is resistance, T is temperature, and α is the thermal coefficient of resistance of the thermometer material. Therefore, the signal voltage across the resistor varies by $$\Delta V_S = \Delta R\, I = \alpha R \Delta T \sqrt{\frac{P}{R}},$$

where $V_S$ is the signal voltage, I is the current through the resistor, and P is power. The thermal noise in each resistor becomes $$V_N = \sqrt{4kTRB} = 1.2 \times 10^{-10}\sqrt{RB}$$

where B is the measurement bandwidth in seconds, R is the resistance in Ohms, and k is Boltzmann's constant. Assuming the detection system can be constructed without introducing noise in excess of the thermal noise, the signal to noise ratio becomes $$S/N = 8.3 \times 10^9 \alpha \Delta T \sqrt{P/B}.$$

Protein-ligand reactions are generally investigated at low concentrations during high-throughput screening, typically in the range of $10^{-5}$ to $10^{-6}$ M. The reactions typically release a heat of reaction, Q, which is on the order of $10^4$ Cal/mole. For illustrative purposes, consider combining 2 drops with concentrations of 2 µM of protein and ligand, respectively. If the drops have equal volumes, the combination has a 1 µM concentration of each reactant. Additionally, $$CV\Delta T = MVQ,$$

where V is the solution volume, C is the heat capacity of the solution, and M is the concentration in the mixed drop. Therefore, $$\Delta T = MQ/C = 10^{-6}\,\text{mole}/L \times 10^4\,\text{Cal/mole}/10^3\,\text{Cal}/^\circ\text{C}.\text{-}L = 10^{-5\circ}\,\text{C.,}$$

where Q is the heat of reaction, C is the heat capacity of the solute, and M is the concentration in the mixed drop.

For example, for a thin film thermometer made from a-Si, for which $\alpha = 2.8 \times 10^{-2\circ}\,\text{C.}^{-1}$, and a bandwidth of 0.1 Hz, a signal to noise ratio of 7 is achieved with 1 µW of power dissipated in the resistor. The voltage change then becomes $$\Delta V_S = 2\Delta RI = 2\alpha \Delta TRI = 4 \times 10^{-7} RI = 4 \times 10^{-7}\sqrt{PR}.$$

The following table provides the signal strength for various exemplary combinations of thermometer impedance and power:

TABLE 2

| Power | Thermometer Impedance | Detection Voltage | S:N |
| --- | --- | --- | --- |
| 1 μW | 100 kΩ | 126 nV | 7:1 |
| 1 μW | 1 MΩ | 400 nV | 7:1 |
| 4 μW | 100 kΩ | 252 nV | 15:1 |
| 4 μW | 1 MΩ | 800 nV | 15:1 |

The values in the table assume 1 μM concentrations of protein and ligand in the solution of the merged drops, $10^4$ cal/mol heat of reaction, and a large enough binding constant such that almost all protein and ligand react, resulting in the 10 μ° C. temperature rise cited above.

To initiate a reaction, the deposited drops need to be merged together and the drop contents well mixed. It is noted that numerous methods for drop deposition are known in the art, any of which may operate beneficially with the present invention for the purpose of dispersing drops.

Although numerous means and methods for merging the deposited drops may be utilized, for the purposes herein, one example method, the methods disclosed in U.S. patent application Ser. No. 10/115,336 ("Apparatus and Method for Using Electrostatic Force to Cause Fluid Movement"), will be briefly described. To reduce complexity of the system and to increase reliability, this example drop merging method utilizes electrostatic forces generated by a planar configuration of two electrodes to merge the two drops and cause equilibration through fast mixing. The electrodes are constructed from thin conducting films on the surface of the device, using standard fabrication techniques, including in embodiments, but not limited to, lithographic patterning of thin films, micro-electronic fabrication techniques (e.g. including sputtering, chemical etching, evaporation), and printed circuit board fabrication techniques.

Figure 6:
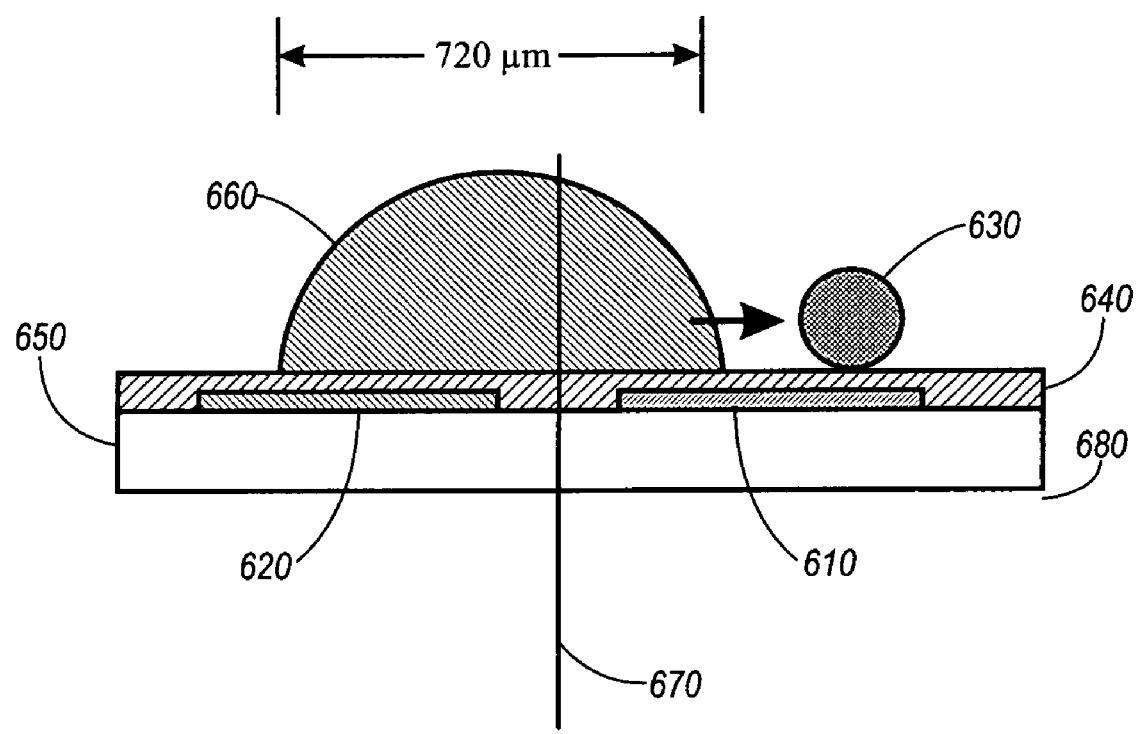
FIG. 6 is an illustration of one method for merging of deposited drops according to the present invention.

Referring now to FIG. 6, the merging electrodes are formed from conducting film 620 and the conducting film 610, which are positioned on the surface of substrate 650 and covered by insulating layer 640. In this example, conducting films 610 and 620 may be approximately 1.0 mm by 0.8 mm in size, with a thickness ranging in size from approximately 0.1 μm to approximately 10 μm, and are separated by a gap of approximately 50 μm and are made of aluminum or copper thin film; the insulating layer may be approximately 0.1 μm to approximately 2 μm in thickness and may, for example, be made of silicon oxide or silicon nitride or silicon oxynitride, or spin-, spray-, or otherwise deposited polymers, such as parylene, Dupont Teflon AF, 3M Fluorad products, 3M EGC 1700, other fluoropolymers, polysiloxanes, diamond-like carbon or other spin-coated, spray-coated, dip coated, or vapor deposited polymers. Suitable insulator materials have a high electrical resistivity, chemical & mechanical durability and have no pinholes in deposited thin film form. For illustrative purposes, also shown is high conductance film 680 that enables thermal equilibration in the thermal equilibration region. Protein drop 660 is deposited asymmetrically across the surface above conducting films 610 and 620 such that the drop disproportionately occupies the surface above one of the conducting films. In this example, 93% of protein drop 660 occupies the surface on the side of meridian 670 above conducting film 620 and 7% of protein drop 660 occupies the surface on the side of meridian 670 above conducting film 610.

Ligand drop 630 is deposited on the surface above conducting film 610. When a voltage is applied, preferably in the form of a voltage pulse, across conducting films 610 and 620, drop 660 is propelled toward stationary drop 630 and the drops merge. While the comparative drop sizes of protein drop 660 and ligand drop 630 may be equal, unequal drop sizes may also be used. The hydrophobic surface of insulating layer 640 the adhesion of drops 630 and 660 to the surface, which reduces the drag on the drops during merging. In this example, the hydrophobic surface is made of a fluorinated polymer, such as, for example, 3M Fluorad, Dupont Teflon AF, 3M EGC-1700, or plasma-deposited fluorocarbons. In one embodiment, a Parylene coating may be used as the insulator layer, as well as for the hydrophobic surface.

Alternatively, in an alternate embodiment, the thermometer material (e.g. amorphous silicon) itself may be utilized to construct drop mover electrodes. In another embodiment, the electrodes and thermometer may be fabricated in different layers, with the electrodes in a layer between the drop deposition points and the thermometer, to enable placing metal drop mover electrodes on top of the thermometers. In this embodiment, an electrically insulating layer separates the thermometers and electrodes.

Several technologies are available for drop delivery, with one of these technologies being syringes. For example, Hydra Microdispensers (made by Robbins Scientific, Sunnyvale, Calif.) dispense liquids into all wells of 96 or 384 microplates simultaneously. As stated by Robbins Scientific in their product information, "The barrels of 96 or 384 syringes are held in a fixed array centered along an X-Y grid that corresponds to the exact center of each well in a microplate. The plungers within the syringes move up and down under computer control, dispensing or aspirating liquids from microplates to the detector array. A precision motor assembly smoothly moves the plungers in increments of 2.5 microns. When equipped with 100 nl syringes, this allows accurate dispensing of volumes as low as 100 nl. For the purposes herein, such a system could be utilized to deliver, for example, 100 nL ligand and 300 nL protein drops.

Cartesian Technologies provides a syringe-based system for delivering drops, wherein the Cartesian system utilizes syringe-syringe pump-solenoid assemblies to accurately aspirate and dispense drops from 20 nL to 250 μL, which is a range sufficient to satisfy the drop size requirement of the present embodiment.

Packard BioSciences markets a system with piezoelectric-driven tips for aspirating liquids and delivering drops. The BioChip Arrayer product is a system with four dispensers (as compared with the full 96 or 384 of the Hydra Dispenser discussed above), and it delivers 300 nL in 2 seconds. If needed, several of these units may be used in parallel to satisfy the requirements of the present invention. Conversely, for embodiments with a much smaller numbers of samples, one unit may be sufficient.

Pin spotting is a technology commonly used to place drops of solution onto slides in the DNA MicroArray industry. Pin spotting is often used for drops much smaller than 100-300 nL, as is common in the DNA MicroArray industry. However, there are some pin spotting technologies that can deliver drops with volumes in the range of 100 nL to 500 nL, as is preferred in an example embodiment of the present invention. For example, V&P Scientific sells pin spotting solutions for drops in this size range.

Figure 7:
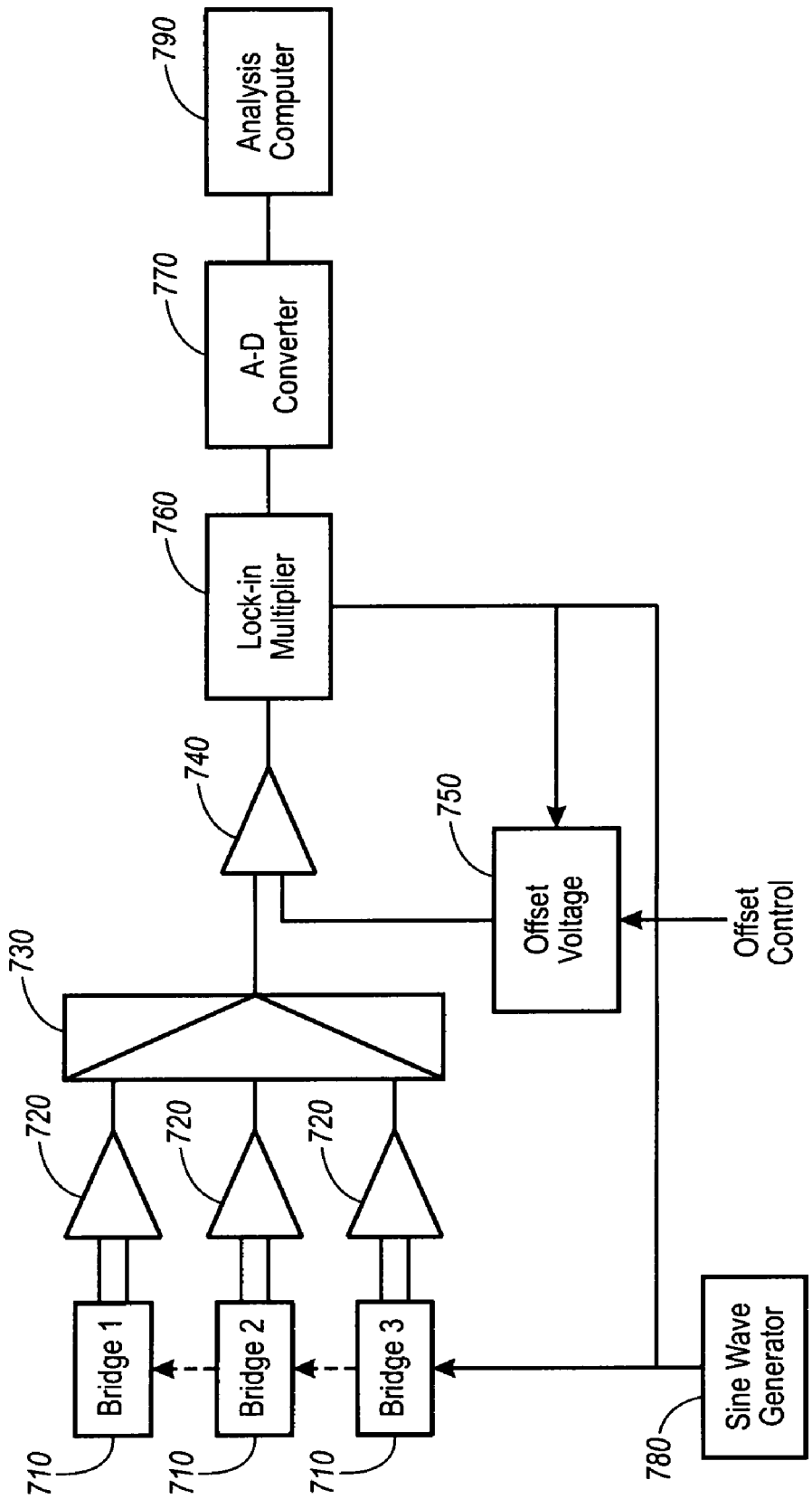
FIG. 7 is a schematic of the electronic measuring system in accordance with the system and method of the present invention.

Referring now to FIG. 7, there is shown a schematic of one example embodiment of the electronic measuring system utilized herein. For the purposes of example, an alternating current (AC) detection method is illustrated. The AC detection method eliminates the 1/f noise inherent in electronic devices, particularly the a-Si thermometer, in which the 1/f noise can be significant at frequencies up to 1 kHz. A bridge circuit is used to detect changes in the resistance of the thermometers. The electronics implements four functions: amplification of the output of the bridge, zeroing of the bridge, detection of the signal, and computer analysis of the signal. For each bridge 710, a sine wave is provided by generator 780. This sine wave drives the two input terminals of each bridge.

Each bridge has two output terminals whose difference represents the temperature difference of the reference and measurement cells of the bridge. The signal on these two terminals is amplified by a low-noise signal amplifier 720. Because the signal level is low, noise introduced by this function must be minimal, but noise minimization must be balanced by design considerations. For example, for the array to be disposable, which is desirable in some applications, the amplifiers must be located off the array, but amplifiers placed on the periphery result in the introduction of noise through the longer lead length. To minimize noise from interconnect, the amplifiers may be placed on a separate temperature-controlled heat sink positioned in close proximity to the detector array, with amplifiers 720 placed directly above the detector array and contacting the array through compressible pogo-pin connectors. An additional advantage of placing each amplifier directly above its associated bridge is that the bridge output signal wires do not have to pass near any other wires thereby reducing noise coupling.

A multiplexor 730 enables several individual detectors to use each lock-in amplifier and digitizer. With the embodiment of the invention shown in FIG. 7, advantage is derived by the use of one amplifier for each detector and placement of the multiplexor 730 after the amplifier. The noise introduced by the multiplexor contributes a smaller relative amount than if the multiplexor had been placed before the signal amplifier. Alternatively, if noise levels permit, the multiplexor could be placed before the signal amplifiers, allowing fewer signal amplifiers and a more compact arrangement of amplifiers and bridges.

The temperature sensors in each bridge may be similar but not identical with each other. After temperature equilibration, the output of the bridge will not quite be zero because of these differences. The output will be a small sine-wave proportional to the difference. This common mode signal, if not reduced, limits the amount of amplification between the bridge and the lock-in amplifier mixer. This in turn limits the system sensitivity. This common mode signal is minimized by use of the bridge zero operation that is performed after the initial amplification through second stage amplifier 740 through offset voltage 750. A control signal selects a proportion of the sine-wave reference signal to be subtracted out of the amplified input signal. This control signal is set by measuring the output after equilibration and set its value to minimize the common mode output. If the inherent balance of the bridge is sufficient, then the offset amplifier is not needed.

A lock-in operation 760 produces a dc output equal to the amplitude of the detector signal and may be implemented through known electronic circuitry. A standard lock-in amplifier known in the art contains an amplifier that increases input signal amplitude. The signal is then filtered by a bandpass filter with a center frequency the same as a reference sine-wave to remove noise at frequencies other than the reference frequency. A reference sine-wave is also input to the circuit. It is converted to a sine-wave and its phase is shifted to correspond to the phase of the input signal. The reference signal is then mixed with the input signal to create a composite output signal with a low-frequency component that represents the signal and a high-frequency component that represents the noise. A low-pass filter removes the high-frequency noise component. Alternatively, the lock-in operation could be implemented in software. The output of the lock-in operation is digitized by A-D converter 770 and input into computer 790 for analysis. The amplitude of this digitized signal represents the temperature difference on the bridge. After the drops are moved together and when a reaction occurs, its amplitude will increase until the drops are fully mixed and then decrease as heat is removed through conduction and evaporation. If no reaction occurs, no significant change will occur in the signal. The computer correlates the digitized signal against the expected temperature increase and decrease. If the correlation is positive, then the occurrence of a reaction is signaled.

Figure 8:
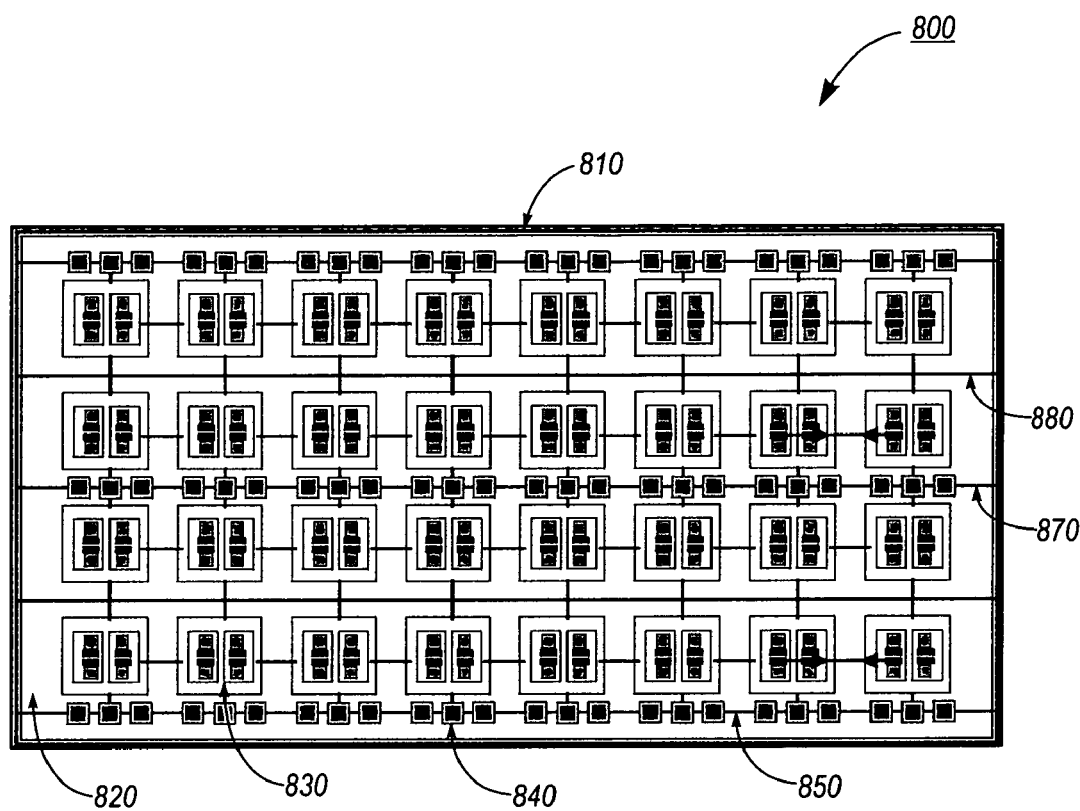
FIG. 8 is a block diagram depicting an array of components of a nanocalorimeter in accordance with another embodiment of the present invention.

Referring now to FIG. 8, in one embodiment of the present invention, the detectors of the detector array are arranged in a rectilinear orientation to form a matrix array. In this example, the array is fabricated on thin plastic sheet 810, for example a 10 μm thick Kapton® plastic substrate, and is supported by heat sink 820, which is made of a material with a high thermal conductivity such as Cu or Al. Thin film conducting lines 850 placed in the regions between individual detectors 830 serve as electrical interconnect that carry signal and power between the detectors and the electronic module on the outside. Detectors 830 require interconnect for the signal excitation and the drop merging electrodes. All detectors in pairs of adjacent rows are connected to common merge-electrode power 880. In embodiments, the resistive thermometers, drop merging electrodes, and electrical interconnect may be patterned on one side of the matrix array, and the thermal equilibration film may be fabricated on the other side. In an embodiment, measurements are made simultaneously in two rows. Detector signal and ground are provided through contact pads located over the heat sink adjacent to each detector and connected to the array through detector amp contact pads 840. Common bridge-excitation is provided for pairs of rows by bridge power conducting lines 870. The merge-electrode power and common bridge-excitation are introduced through alternating rows. Because it is desirable to transfer fluids from standard storage devices, such as well-plates having different densities (96 well, 384 well, or 1536 well) the detectors have the same 9 mm square layout as standard 96 well-plates used in the biotechnology and pharmaceutical industries.

Figure 9:
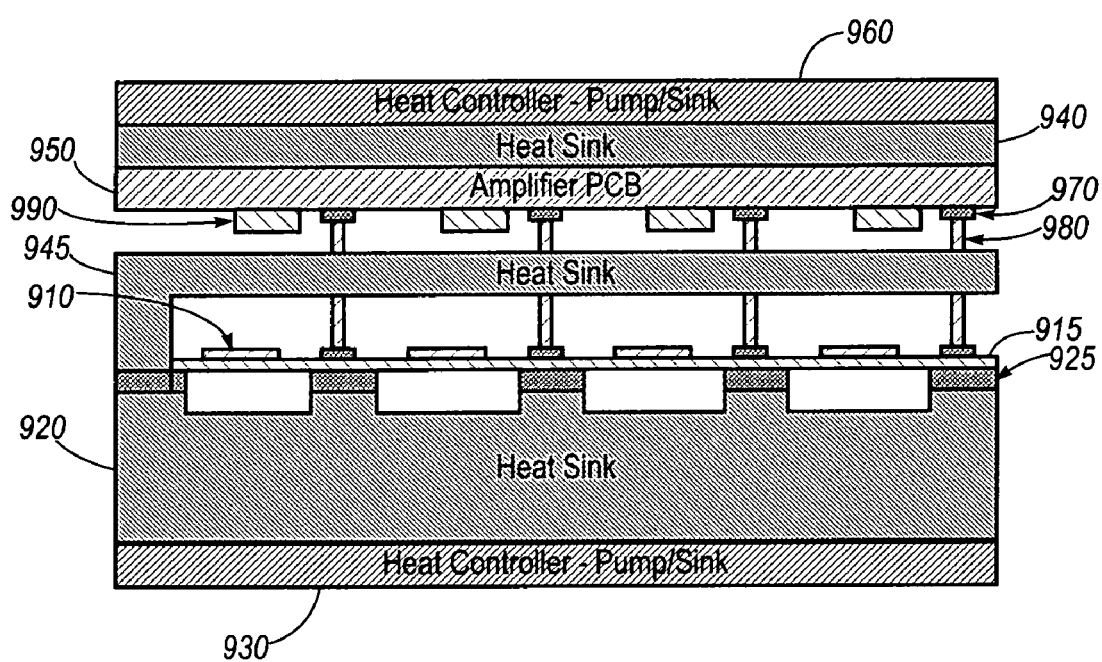
FIG. 9 is a cross-sectional diagram illustrating the operating environment of the nanocalorimeter in accordance with an embodiment of the present invention.

Referring now to FIG. 9, there is shown an example cross-section of the nanocalorimeter assembly and its detector environment, which provides thermal isolation, electrical connections and sample delivery. To achieve thermal isolation, the environment is structured to insure that the heat transferred to or from the drop is inconsequential. The three main heat transfer channels for the assembly include: thermal conduction through the air, thermal conduction across the supporting medium, and evaporation. In embodiments, measurements can be conducted at low temperatures and high humidities, for example 5° C. in near 100% relative humidity (preferably noncondensing), to reduce evaporation to acceptable limits. Specifically, evaporation is controlled in part by maintaining near 100% relative humidity, within some acceptable tolerance, of the solvent used to dissolve the chemicals being investigated. This may be accomplished by exposing a reservoir of solvent to the atmosphere in the chamber enclosing the detector. The lower temperature reduces the vapor pressure of the solvent, and higher humidities reduce the concentration gradient of solvent in the gas phase near the surface of the drop, thereby reducing the driving force for evaporation.

In other embodiments, reasonable measurements might be attainable at higher temperatures or higher humidities despite the correspondingly higher evaporation rates, in which cases operation at low temperatures or high humidities may not be necessary. Thermal conductivity through the surrounding environment can be reduced in embodiments through use of a controlled atmosphere, for example an environment rich in Xenon or Argon, which have lower thermal conductivities than air. In embodiments, conductivity can also be controlled through the use of a partial or complete vacuum, aerogels or other insulating materials, and other methods that will occur to those skilled in the art.

To minimize thermal conduction across the supporting medium, detector 910 resides on substrate 915, which is supported by substrate carrier 925, which is in contact with heat sink 920. In this example heat sink 920 is comprised of copper, but other materials known in the art could also be utilized. In embodiments heat sink 920 may be in thermal contact with an optional active temperature control device 930, which controls the temperature of the heat sink to within 1 m° C. to 0.1° C. of amplifier heat sink 940. The detector amplifiers dissipate power (10 mW each), which may be too much heat for the detector heat sink in some embodiments. The amplifier power can be sunk to a separate heat sink if desired. Signal amplifiers 990 reside on amplifier printed circuit board 950, which is in contact with heat sink 940. The temperature of heat sink 940 can be controlled by a temperature control device 960, if desired for a particular embodiment. Pogo pin connectors 980 connect amplifier printed circuit board 950 with detector substrate 915 through amplifier pads 970. There are several conditions in which the heat sink 920 does not need to be temperature controlled. In these cases, the heat sink is thermally isolated from the enclosing chamber using standard low conduction materials like glass, plastic or stainless steel tubing. In these cases, the Amplifier PCB 950 is placed in direct contact with the temperature controlled enclosing chamber.

To better appreciate the magnitude of temperature fluctuations that heat sink 920 may experience due to fluctuations of the chamber wall, the heat capacity for various copper heat sinks corresponding to various array sizes is shown in the table below. For the purposes of the table, all heat sinks are 3 cm in thickness. The heat sink area is shown below for the different examples, and the heat sink is assumed to be separated by 10 cm from the chamber walls, with Xenon gas at about 0.1 to 2 atm filling the space.

would change the heat sink by 2 μ° C. over a 10 second measurement. Note that since the measurement is differential, as both the measurement and reference thermometers change by the same amount providing common mode rejection, and since the chamber walls can be controlled to 0.1° C. with variations that are not rapid, the heat sink provides more than adequate temperature stability from conduction to the wall. Because the electrical connection to the detector array increases the thermal conduction between the heat sink and the chamber wall, conductance down the leads may be actively controlled in embodiments by placing the leads in thermal contact with an intermediate heat sink 945 whose temperature is actively controlled to be equal to that of the heat sink.

To better appreciate the magnitude of temperature fluctuations that heat sink 920 may experience due to heat conduction through the Pogo pins, an example of Pogo pins contacting a 384-detector array is considered in the table below. Pogo-pin connector 980 materials, for example brass, are selected for thermal performance. In this example, the power conducted per pin for a 0.1 C temperature difference across the pin is shown in the following table along with the total power conducted for a 384-detector array (assuming three pins for each detector) for a 0.1° C. and a 0.1 m° C. temperature difference across the pin. For the purposes of the calculations shown in the table, a circular contact area with a diameter of 10 μm is assumed. To minimize the area of contact, the pogo pins may be the pointed-tip type. The temperature change during a 10 second measurement time is also shown. To keep the temperature change sufficiently low, the temperature of amplifier printed circuit board 950 is accurately controlled in embodiments, either through active control or by thermal contact with the chamber wall. For example, to limit the temperature rise ΔT of heat sink 920 to 13 μ° C. or less over 10 seconds, the values in Table 4 show that the temperature of the amplifier printed circuit board 950 must be controlled to within 0.01° C. Such control is possible using known active temperature control elements, such as Peltier devices, a circulating-fluid refrigeration system, a heat pump, or any of a number of other active temperature-control devices known by those skilled in the art. Alternatively, if the

TABLE 3

| Well Number | Array Design | Array Size | Heat Capacity | Sink Area | Time Constant |
|---|---|---|---|---|---|
| 96 | 12 × 8 | 14.8 cm × 11.2 cm | 1500 J/C. | 485 cm$^2$ | 515000 sec |
| 384 | 24 × 16 | 25.6 cm × 19.4 cm | 4500 J/C. | 1263 cm$^2$ | 594000 sec |
| 1536 | 48 × 32 | 47.2 cm × 32.8 cm | 14000 J/C. | 2030 cm$^2$ | 1150000 sec |

As shown in the table, with the smallest time constant over 500,000 seconds, a small 0.1° C. step-change temperature difference between the array heat sink and the chamber wall chamber wall is controlled to within 0.01° C., then thermal contact of the amplifier printed circuit board with the chamber wall is sufficient to limit ΔT to 13 μ° C.

TABLE 4

| | Power/Pin (0.1 C. control) | Total Power (0.1 C. control) | ΔT in 10 sec (0.1 C. control) | Total Power (0.1 mC. control) | ΔT in 10 sec (0.1 mC. control) |
|---|---|---|---|---|---|
| 1.2 cm pin | 49.2 μW | 56.6 mW | 0.13 mC. | 56.6 μW | 0.13 μC. |
| 0.56 cm pin | 47.7 μW | 54.9 mW | 0.12 mC. | 54.9 μW | 0.12 μC. |

Figure 10:
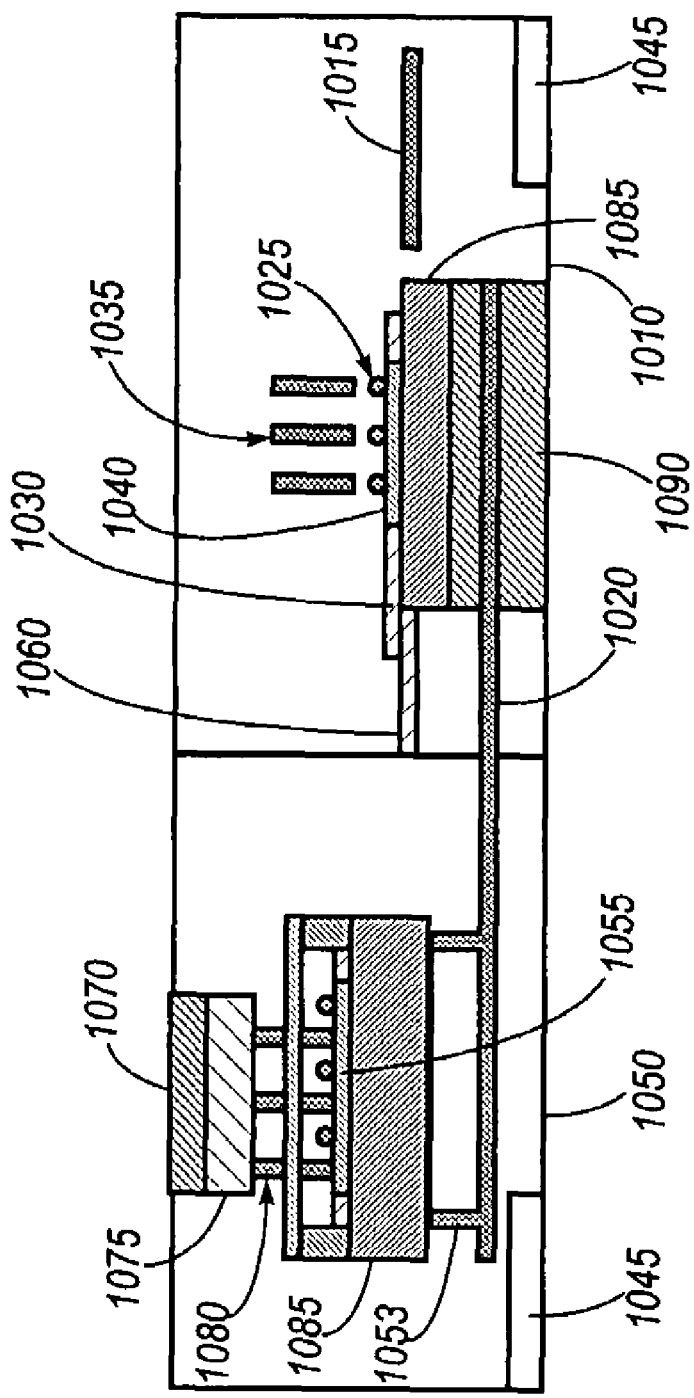
FIG. 10 is a cross-sectional diagram illustrating one embodiment of the process flow of the nanocalorimeter in accordance with the present invention.

FIG. 10 illustrates a cross section of the measurement system utilizing the array described herein. The measurement system in this example configuration includes two compartments, load lock chamber 1010 and measurement chamber 1050. The chambers and the atmosphere contained within them are equivalent; they are at the same operating temperature. The atmosphere within each chamber is a non-reactive gas, for example xenon, argon, air, or nitrogen, at a near 100% relative humidity for the solvents used in the drops being measured, and this humidity level is maintained through use of vapor pressure reservoirs 1045. The temperature of the chamber walls is controlled to within 0.1° C. Heat sink 1085 receives heat from the power dissipated in the measurement thermometers on detector array 1040 when in the measurement chamber 1050. In this example four thermometers are used for each detector, as shown in FIG. 1, and each thermometer dissipates approximately 4 μW. The rate of temperature increase of the heat sink due to thermometer heating is approximately 10 μ C. during a 10 second measurement, based on a 96 detector array and a heat sink with a heat capacity of 1500 J/°C. (refer to Table 3 above). Detector array 1040 is connected to detector array electronics 1030 which in turn are connected to system electronics 1060. Biomaterials are contained within a biomaterial storage well plate 1015, which is placed in the load lock chamber 1010. In the measurement chamber 1050 are detector electronics 1075 as well as the associated heat sink/controller 1070 for the detector electronics.

Biomaterials 1025 are deposited on the array with chemical deposition device 1035 in preparation for the measurement. While in the load lock chamber 1010, the heat sink 1085 and associated detector 1040 and biomaterials 1025 are brought into thermal equilibrium with the chamber through heat conductor 1090. Heat conductor 1090 may be any material or system of high thermal conductivity, and may be, for example, a metal block such as copper or aluminum that is in good thermal contact with both the chamber wall and the heat sink 1085. As shown in FIG. 10, thermal contact of heat conductor 1090 with heat sink 1085 occurs through the array transporter 1020. However, this configuration is exemplary only; other configurations will occur to those skilled in the art and are contemplated by the disclosure herein.

In alternative embodiments, heat conductor 1090 may have active temperature control, such as control by a circulating-fluid refrigeration or heating system, a Peltier device, a resistive heater, a heat pump, or any of a number of other active temperature-control devices known by those skilled in the art. Furthermore, in alternative embodiments the heat conductor and associated temperature control function can be integrated into the array transporter 1020. Array transporter 1020 moves a detector array with deposited biomaterials from the load lock into measurement chamber 1050 and, in this example, utilizes a circular motion so that a detector array with measured materials is simultaneously moved from the measurement chamber to the load lock. Other array transport methods may be utilized, such as pick-and-place devices and belt devices with elevators.

Once in the measurement chamber, the detector array is raised into contact with the Pogo pins, and simultaneously the heat sink 1085 is raised above the transporter 1020 and thermally isolated from it by supporting pins 1053. The supporting pins may be fabricated from any good thermal insulating material with sufficient mechanical strength, such as glass rods, stainless steel hollow tubing, plastic rods, porous ceramics, and other materials known to those skilled in the art. Other configurations are possible; for example, in alternative embodiments a temperature controller may be used to maintain heat sink 1085 at a specified temperature in measurement chamber 1050, for example within 1 m° C. of the temperature of heat sink/controller 1070 of detector electronics 1075, rather than relying on thermal isolation alone. Pogo pin detector connectors 1080 make electrical contact directly to the detectors to transmit thermal change information from the detector array to detector electronics 1075. This type of connector is used in this example to provide a nonpermanent connection that allows connection to be made to successive arrays with low thermal contact to the array and good placement accuracy with a small foot-print that provides symmetrical contact to the measurement and reference regions to enable precise differential measurements.

In operation, detector array 1040, whose initial temperature is within 1° C. of the temperature of load lock chamber 1010, is placed in load lock chamber 1010 while a previously set-up detector array 1055 is being measured in measurement chamber 1050. The proximity of measurement chamber 1050 to load lock chamber 1010 enables the connected detector array to be moved between the chambers while remaining in a controlled environment. Biomaterials are then moved into load lock chamber 1010 and stored in an appropriate vehicle 1015, such as a 384 or 1536 well plate, although other containers or well plate sizes would also be appropriate. Biomaterials 1025 are then deposited on detector array 1040 using, for example, an aspirating/printing system or an automated syringe-type loader 1035. Deposition device 1035 is maintained at a controlled temperature to avoid warming biomaterials 1025. Initially, detector array 1040 is connected to detector array electronics 1030 and system electronics connector 1060, which provides the necessary electrical connections to all the detector elements in detector array 1040 with the exception of the detector electronics for the measurement bridge. Depending on conditions, the detector bridges in detector array 1040 may be driven by the AC sine wave (for example, element 560 in FIG. 5) to self-heat to a temperature that equilibrates the drop temperature with the controlled environment in the load lock chamber. This signal is conducted through the system electronics connector 1060 to the detector array electronics 1030.

After the deposited materials 1025 come to thermal equilibrium with the detector array 1040, the detector array 1040 with deposited chemicals 1025 is then moved from load lock chamber 1010 to measurement chamber 1050 by array transporter 1020 and measured detector array 1055 is moved into load lock chamber 1010. This movement may be accomplished through a rotation, such as a 180-degree rotation, or by any other means known in the art. Within measurement chamber 1050, the detector array is in thermal contact with heat sink 1085, which in this embodiment is thermally isolated from transporter 1020 by supporting pins 1053 in measurement chamber 1050. The measurement sequence is initiated by applying the AC-sine wave to the detector bridges. This signal is created by an AC generator located on the amplifier printed circuit board 1075 and conducted to detector array 1055 through the pogo pins 1080. The detector bridge is then zeroed by properly setting the offset voltage. Thermal equilibration is confirmed by measuring the voltage across the detector bridge for a short period of time. When the rate of change of this voltage is below a pre-specified level, the system is in thermal equilibrium. The zeroing operation may need to be repeated during this process.

A row of drops of deposited chemicals 1025 is then merged and mixed on the surface of the detector array. This is accomplished by applying a drop moving voltage from the amplifier printed circuit board 1075 through the pogo pins 1080 to the detector array 1055. The transient voltages generated from the merging voltages are allowed to dissipate. The reaction during mixing is then measured by detecting the imbalance in the bridge. Each bridge in the row is measured repeatedly for a period of time and the data is input into the computer for analysis.

The individual bridges in a single row may be multiplexed in the detection electronics. A measurement is made on one detector and then the next detector in the row until all the detectors in the row have been measured. This is repeated for a period of time until all measurements for the row are complete. Alternatively, multiple instances of the detection electronics can simultaneously measure all the detector arrays in the row. To further reduce measurement time, measurements may be performed in blocks of two or more rows.

While the present invention has been illustrated and described with reference to specific embodiments, further modification and improvements will occur to those skilled in the art. It is to be understood, therefore, that this invention is not limited to the particular forms illustrated and that it is intended in the appended claims to embrace all alternatives, modifications, and variations which do not depart from the spirit and scope of this invention.

What is claimed is:

1. A method for detecting chemical reactions using a nanocalorimeter comprising a substrate, at least one thermal isolation region residing on the substrate, at least one thermal equilibration region residing within a thermal isolation region, and at least one thermal measurement device residing within each thermal equilibration region, wherein said thermal measurement device is connected to detection electronics; for a thermal equilibration region in a thermal isolation region on the substrate, the method comprising:
   depositing drops of potentially reactive chemical solutions within the thermal equilibration region in the thermal isolation region;
   merging said potentially reactive solution drops, wherein merging said potentially reactive solution drops is accomplished by at least two drop merging electrodes residing within said thermal isolation region; and
   measuring a thermal change occurring within said merged solution drops, the act of depositing drops comprising:
   depositing first and second drops of potentially reactive chemical solutions on a surface within the thermal equilibration region; the first and second drops each having a volume of approximately 20 nL or more;
   the act of merging comprising:
   operating the drop merging electrodes to merge the first and second drops into a mixture on the surface, the mixture including less than 500 µL of volume;
   the act of measuring comprising:
   conducting temperature from the mixture on the surface to a thermal measurement device that is within the thermal isolation region and separated from the drop merging electrodes; the thermal measurement device having an electrical characteristic value that changes in response to change in temperature conducted from the mixture and that can be used to detect thermal change from chemical reaction in the mixture;
   the act of conducting temperature comprising one of:
   conducting temperature from the mixture laterally across the nanocalorimeter's substrate through a thermally conductive structure that extends over the thermal equilibration region; the thermal measurement device being laterally separated from the drop merging electrodes; and
   conducting temperature from the mixture through a thickness of an electrically insulating layer that, in the thermal isolation region, is between the drop merging electrodes and the thermal measurement device, the drop merging electrodes being between the surface and the thermal measurement device, the thermal measurement device being separated from the drop merging electrodes by the electrically insulating layer.

2. The method for detecting chemical reactions using a nanocalorimeter according to claim 1, in which the nanocalorimeter includes a detector array on the substrate, the detector array including the at least one thermal isolation region; the method further comprising:
   providing a controlled environment, said controlled environment including at least one chamber;
   connecting the detector array to the detection electronics;
   connecting the detector array to system electronics for said controlled environment;
   placing the detector array within a first chamber;
   placing the detector array in thermal contact with a heat sink; and
   bringing the detector array to thermal equilibrium within said first chamber;
the act of depositing the first and second drops comprising, with the detector array at thermal equilibrium within the first chamber:
   depositing at least one drop of a first chemical material within each of a measurement region and a reference region;
   depositing at least one drop of a test chemical material within said measurement region; and
   depositing at least one drop of a non-reactive chemical material within said reference region;
the method further comprising:
   bringing the detector array with said drops of chemical materials to thermal equilibrium within said first chamber;
the act of merging further comprising:
   merging said drop of said first chemical material and said drop of said test chemical material within said measurement region; and
   merging said drop of said first chemical material and said drop of said non-reaction material within said reference region;
the act of measuring further comprising:
   measuring a reaction between said drops of said chemical materials with the detection electronics.

3. The method for detecting chemical reactions using a nanocalorimeter according to claim 2, wherein merging said drops of said first chemical material and said drops of said test chemical material and said drops of said first chemical material and said non-reactive material comprises utilizing electrostatic force.

4. The method for detecting chemical reactions using a nanocalorimeter according to claim 2, wherein said at least one chamber comprises at least two chambers.

5. The method for detecting chemical reactions using a nanocalorimeter according to claim 2, wherein said controlled environment provides thermal isolation, electrical connections, and delivery of chemical samples and comprises:
   at least one load lock chamber; and
   at least one measurement chamber.

6. A method of using nanocalorimeters that include substrates, the method comprising:
   depositing first and second drops on a first surface within a thermally isolated region of a nanocalorimeter's substrate; the first and second drops each having a volume of approximately 20 nL or more;

operating electrodes within the thermally isolated region to merge the first and second drops into a mixture on the first surface, the mixture including less than 500 µL of volume; and conducting temperature from the mixture on the first surface to a thermal measurement device that is within the thermally isolated region and separated from the electrodes; the thermal measurement device having an electrical characteristic value that changes in response to change in temperature conducted from the mixture and that can be used to detect thermal change from chemical reaction in the mixture;

the act of conducting the temperature comprising one of:

conducting the temperature from the mixture laterally across the nanocalorimeter's substrate through a thermally conductive structure that extends over a thermal equilibration region within the thermally isolated region; the thermal measurement device being laterally separated from the electrodes; and conducting the temperature from the mixture through a thickness of an electrically insulating layer that, in the thermally isolated region, is between the electrodes and the thermal measurement device, the electrodes being between the first surface and the thermal measurement device, the thermal measurement device being separated from the electrodes by the electrically insulating layer.

7. A method of using nanocalorimeters that include substrates, the method comprising:

depositing first and second sets of drops on first and second surface regions of a nanocalorimeter's substrate, respectively; each drop in the first and second sets having a volume of approximately 20 nL or more;

operating first and second sets of electrodes to merge the first and second sets of drops into first and second mixtures on the first and second surface regions, respectively; each of the first and second mixtures including less than 500 µL of volume; the first mixture being a non-reactive reference mixture and the second mixture being a measurement mixture that includes a test ligand and a target molecule;

maintaining the second mixture under appropriate conditions and for a sufficient time to allow binding of the test ligand to the target molecule;

conducting a first temperature received from the first mixture from the first surface region to a first set of resistive thermometers and conducting a second temperature received from the second mixture from the second surface region to a second set of resistive thermometers; the first set of resistive thermometers having a first set of electrical resistances in response to the first temperature and the second set of resistive thermometers having a second set of electrical resistances in response to the second temperature; and using the first and second sets of electrical resistances to electrically detect difference between the first and second temperatures, the difference indicating whether a chemical reaction occurred between the test ligand and the target molecule in the second mixture.

8. The method of claim 6 in which the thermal measurement device is over the first surface of the substrate and spaced apart from the electrodes; the substrate having a thickness between the first surface and a second surface opposite the first surface; the nanocalorimeter including a thermally conductive structure on the second surface, having thermal contact through the substrate with the first surface and having thermal contact through the substrate with the thermal measurement device; the act of conducting the temperature including:

conducting the temperature from the mixture through the substrate to the thermally conductive structure;

conducting the temperature laterally through the thermally conductive structure; and conducting the temperature from the thermally conductive structure through the substrate to the thermal measurement device.

9. The method of claim 6 in which the act of conducting the temperature includes conducting the temperature from the mixture through a thickness of an electrically insulating layer that, in the thermally isolated region, is between the electrodes and the thermal measurement device, the electrodes being between the first surface and the thermal measurement device, the thermal measurement device being separated from the electrodes by the electrically insulating layer; the electrodes being positioned over the thermal measurement device.

10. The method of claim 7 in which the first and second surface regions are a reference region and a measurement region, respectively.

11. The method of claim 7 in which an electrically insulating layer is between the first and second sets of electrodes and the first and second sets of resistive thermometers, such that the first and second sets of electrodes are positioned over the first and second sets of resistive thermometers, respectively; the act of conducting the first temperature and the second temperature comprising:

conducting the first temperature from the first mixture through the electrically insulating layer to the first set of resistive thermometers and conducting the second temperature from the second mixture through the electrically insulating layer to the second set of resistive thermometers.

12. The method of claim 7 in which the first and second surface regions are thermally isolated regions of the substrate with first and second equilibration regions within the first and second surface regions, respectively; the act of conducting the first and second temperatures comprising:

conducting the first temperature through a first thermally conductive structure that extends over the first thermal equilibration region and conducting the second temperature through a second thermally conductive structure that extends over the second thermal equilibration region.

13. The method of claim 7 in which the first and second surface regions are on a first surface of the substrate, the first and second sets of resistive thermometers being over the first surface of the substrate and being spaced apart from the first and second surface regions, respectively; the substrate having a thickness between the first surface and a second surface opposite the first surface; the nanocalorimeter including first and second thermally conductive structures on the second surface, the first thermally conductive structure having thermal contact through the substrate with the first surface region and having thermal contact through the substrate with the first set of resistive thermometers, the second thermally conductive structure having thermal contact through the substrate with the second surface region and having thermal contact through the substrate with the second set of resistive thermometers; the act of conducting the first and second temperatures comprising:

conducting the first temperature from the first mixture through the substrate to the first thermally conductive structure and conducting the second temperature from the second mixture through the substrate to the second thermally conductive structure;

conducting the first temperature through the first thermally conductive structure laterally and conducting the second temperature through the second thermally conductive structure laterally; and conducting the first temperature from the first thermally conductive structure through the substrate to the first set of resistive thermometers and conducting the second temperature from the second thermally conductive structure through the substrate to the second set of resistive thermometers.

14. A method for detecting chemical reactions using a nanocalorimeter comprising a substrate, at least one thermal isolation region residing on the substrate, at least one thermal equilibration region residing within a thermal isolation region, and at least one thermal measurement device residing within each thermal equilibration region, wherein said thermal measurement device is connected to detection electronics; for a thermal equilibration region in a thermal isolation region on the substrate, the method comprising:

depositing drops of potentially reactive chemical solutions within the thermal equilibration region in the thermal isolation region;

merging said potentially reactive solution drops, wherein merging said potentially reactive solution drops is accomplished by at least two drop merging electrodes residing within said thermal isolation region; and measuring a thermal change occurring within said merged solution drops, and wherein the nanocalorimeter further includes a second thermal equilibration region in addition to the first above-mentioned thermal equilibration region, second drop merging electrodes in addition to the first above-mentioned drop merging electrodes, and a second thermal measurement device in addition to the first above-mentioned thermal measurement device; the first and second thermal measurement devices including first and second sets of resistive thermometers, respectively; the act of depositing drops comprising:

depositing first and second sets of drops on first and second surface regions of the first and second thermal equilibration regions, respectively; each drop in the first and second sets having a volume of approximately 20 nL or more;

the act of merging comprising:

operating the first and second drop merging electrodes to merge the first and second sets of drops into first and second mixtures on the first and second surface regions, respectively; each of the first and second mixtures including less than 500 µL of volume; the first mixture being a measurement mixture that includes a test ligand and a target molecule and the second mixture being a non-reactive reference mixture;

the act of measuring comprising:

maintaining the first mixture under appropriate conditions and for a sufficient time to allow binding of the test ligand to the target molecule;

conducting a first temperature received from the first mixture from the first surface region to the first set of resistive thermometers and conducting a second temperature received from the second mixture from the second surface region to the second set of resistive thermometers; the first set of resistive thermometers having a first set of electrical resistances in response to the first temperature and the second set of resistive thermometers having a second set of electrical resistances in response to the second temperature; and using the first and second sets of electrical resistances to electrically detect difference between the first and second temperatures, the difference indicating whether a chemical reaction occurred between the test ligand and the target molecule in the first mixture.

15. A method for detecting chemical reactions using a nanocalorimeter comprising a substrate, at least one thermal isolation region residing on the substrate, at least one thermal equilibration region residing within a thermal isolation region, and at least one thermal measurement device residing within each thermal equilibration region, wherein said thermal measurement device is connected to detection electronics; for a thermal equilibration region in a thermal isolation region on the substrate, the method comprising:

depositing drops of potentially reactive chemical solutions within the thermal equilibration region in the thermal isolation region;

merging said potentially reactive solution drops, wherein merging said potentially reactive solution drops is accomplished by at least two drop merging electrodes residing within said thermal isolation region; and measuring a thermal change occurring within said merged solution drops, the act of depositing drops comprising:

depositing the drops of potentially reactive chemical solutions on a surface within the thermal equilibration region;

the act of merging comprising:

providing signals to the drop merging electrodes to cause the drops to merge on the surface;

the act of measuring a thermal change comprising:

thermally conducting the thermal change from the surface to the at least one thermal measurement device within the thermal isolation region; and detecting electrical change at each thermal measurement device within the thermal isolation region, the electrical change indicating the thermal change.

16. A method for detecting chemical reactions using a nanocalorimeter comprising a substrate, at least one thermal isolation region residing on the substrate, at least one thermal equilibration region residing within a thermal isolation region, and at least one thermal measurement device residing within each thermal equilibration region, wherein said thermal measurement device is connected to detection electronics; for a thermal equilibration region in a thermal isolation region on the substrate, the method comprising:

depositing drops of potentially reactive chemical solutions within the thermal equilibration region in the thermal isolation region;

merging said potentially reactive solution drops, wherein merging said potentially reactive solution drops is accomplished by at least two drop merging electrodes residing within said thermal isolation region; and measuring a thermal change occurring within said merged solution drops, and wherein the nanocalorimeter includes an array of detectors on the substrate, each of the detectors including one or more respective thermal isolation regions that include respective first and second thermal equilibrium regions, the respective thermal isolation regions of a first one of the detectors including the at least one thermal isolation region; the act of depositing drops comprising:

depositing the drops of potentially reactive chemical solutions on respective first and second surfaces within the respective first and second thermal equilibrium regions of two or more of the detectors;

the act of merging comprising, for each of the two or more detectors:

providing signals to respective drop merging electrodes adjacent the respective first and second surfaces, causing the drops on each of the first and second surfaces to merge;

the act of measuring a thermal change comprising, for each of the two or more detectors:

thermally conducting thermal change from the respective first and second surfaces to respective thermal measurement devices; and detecting electrical change at each thermal measurement device, the electrical change indicating thermal change.

* * * * *